US010832810B2

(12) United States Patent
Gulzar

(10) Patent No.: US 10,832,810 B2
(45) Date of Patent: Nov. 10, 2020

(54) MANAGED SERVICE PROVIDER SYSTEM FOR COLLABORATIVE HEALTHCARE CREDENTIALING, COMPLIANCE, AND SCHEDULING ACROSS SHARED SUPPLIERS

(71) Applicant: Nadir Gulzar, Fremont, CA (US)

(72) Inventor: Nadir Gulzar, Fremont, CA (US)

( * ) Notice: Subject to any disclaimer, the term of this patent is extended or adjusted under 35 U.S.C. 154(b) by 380 days.

(21) Appl. No.: 15/479,208

(22) Filed: Apr. 4, 2017

(65) Prior Publication Data

US 2017/0300640 A1   Oct. 19, 2017

Related U.S. Application Data

(60) Provisional application No. 62/322,331, filed on Apr. 14, 2016.

(51) Int. Cl.
  *G16H 50/20*   (2018.01)
  *G06Q 10/10*   (2012.01)
  *G16H 40/20*   (2018.01)

(52) U.S. Cl.
  CPC ........ *G16H 40/20* (2018.01); *G06Q 10/1053* (2013.01); *G06Q 10/1093* (2013.01)

(58) Field of Classification Search
  CPC .......... G16Q 10/1053; G16Q 10/1093; G16Q 10/00; G16H 40/20; G06F 17/60

(Continued)

(56) References Cited

U.S. PATENT DOCUMENTS

| 8,229,761 B2 * | 7/2012 | Backhaus ............. G06Q 10/06 705/2 |
| 2004/0204948 A1 * | 10/2004 | Singletary ............. G06Q 10/10 705/321 |

(Continued)

*Primary Examiner* — Aryan E Weisenfeld
*Assistant Examiner* — Alaaeldin M Elshaer
(74) *Attorney, Agent, or Firm* — Creso Legal LLP

(57) ABSTRACT

A MSP platform provides contingent healthcare worker recruiting and shift assignation in a multilayered process of job order broadcasting, competency matching, proposals from healthcare agencies aka vendors, screening, compliance management, and onboard of each candidate. Each staff profile submitted has to go through multilayered review, approval, and orientation process. Additionally, each healthcare worker's calendar, credential, and compliance have to be managed across multiple employers to prevent scheduling conflict and compliance violations, and guaranteeing full visibility of all healthcare workers across the entire supply chain. MSPs (Managed Service Providers) have the ability to service a large number of facilities on whose behalf the MSPs generate job orders for contingent workforce, and manage fulfillment using suppliers (aka vendors) mapped to the facility being serviced. The supplier ecosystem is a cohesive block that may be shared across all MSPs, and several such MSP ecosystems should be allowed to coexist in the system. Suppliers can be tiered by geography allowing a large vendor network to track demand from one or more healthcare facilities across a single location or a group of vendor locations. Additionally, a facility that is part of an MSP should also be able to work directly with all suppliers either in conjunction with or independent of an MSP. Both long term assignments referred to as 'Travel' position, and on-demand shift assignments referred to as 'Day-to-day' position are serviceable under this centrally available software commonly referred to as 'Software as a Service'.

20 Claims, 39 Drawing Sheets

(58) Field of Classification Search
USPC .......................................................... 705/2, 3
See application file for complete search history.

(56) References Cited

U.S. PATENT DOCUMENTS

| | | | |
|---|---|---|---|
| 2006/0031109 A1* | 2/2006 | LaRue, Jr. ............. | G06Q 10/06 705/7.14 |
| 2007/0021982 A1* | 1/2007 | Sun ........................ | G06Q 10/06 705/2 |
| 2008/0027783 A1* | 1/2008 | Hughes .................. | G06Q 10/00 705/7.14 |
| 2011/0055099 A1* | 3/2011 | Paul ....................... | G06Q 10/00 705/321 |

* cited by examiner

| MSP: Bay Area MSP | | | | | | | | |
|---|---|---|---|---|---|---|---|---|
| Requisitions | | | Sort by | Facility A-to-Z | | 702 → Create Requisition | | Onboard All Submissions |
| State | Facility | Department | | Requisition # | Class | Class | Contract | Status |
| Select... | Select Facility | Select Single Facility | | Enter 3 characters | Select Class | | D2D & Travel | Request for Ca... Go |
| Facility | Department | Requisition # | | Class | Start | | Broadcasted | Actions |
| Holy Cross Hospital, CA | CARDIOLOGY Shift Type: Variable Contract: Travel | TRA-CARD-CNA-001 Created On: Jan 19, 2016 By: Joe Smith Onboard Submitted Profile(s) [0] | | CNA | January 31 2016 | | 0 Agencies | ⊗ Cancel ⊚ Broadcast More ✎ Edit 🔒 Hold Requisition |
| Holy Cross Hospital, CA | CARDIOLOGY Shift Type: Day Contract: Travel | TRAVEL-656 Created On: Mar 21, 2016 By: Joe Smith Onboard Submitted Profile(s) [0] | | RN | April 30 2016 | | 7 Agencies | ⊗ Cancel ⊚ Broadcast More ✎ Edit 🔒 Hold Requisition 🔔 Send Reminder |
| Holy Cross Hospital, CA | CRITICAL CARE Shift Type: Variable Contract: Day to Day | D2D-DEPT-2015-DEC-004 Created On: Dec 28, 2015 By: Joe Smith Onboard Submitted Profile(s) [0] | | CNA | | | 1 Agency | ⊗ Cancel ⊚ Broadcast More ✎ Edit 🔒 Hold Requisition 🔔 Send Reminder |
| Holy Cross Hospital, CA | CRITICAL CARE Shift Type: Variable Contract: Travel | D2D-DEPT-2015-DEC-003 Created On: Dec 18, 2015 By: Nelson R | | RN | December 01 2015 | | 3 Agencies | ⊗ Cancel ⊚ Broadcast More ✎ Edit 🔓 Unhold Requisition 🔔 Send Reminder |
| Holy Cross Hospital, CA | ICTU Shift Type: Variable Contract: Travel | TRA-CLS-ICTU Created On: Jan 19, 2016 By: Joe Smith Onboard Submitted Profile(s) [0] | | CLS | January 20 2016 | | 0 Agencies | ⊗ Cancel ⊚ Broadcast More ✎ Edit 🔒 Hold Requisition |
| Holy Cross Hospital, CA | IMAGING Shift Type: Variable Contract: Travel | TRA-IMG-001 Created On: Dec 24, 2015 By: Joe Smith Onboard Submitted Profile(s) [0] | | CT | January 01 2016 | | 8 Agencies | ⊗ Cancel ⊚ Broadcast More ✎ Edit 🔒 Hold Requisition 🔔 Send Reminder |

Figure 7

Requisitions

| State | | Sort by | Urgent Attention | |
|---|---|---|---|---|
| Select State | | | | |
| Facility | Class | Contract | Status | |
| Select Facility | | D2D & Travel | Open | Go |

| Facility | Department | Class | Requisition# | Start | Proposed | Rate | Action/Status |
|---|---|---|---|---|---|---|---|
| Holy Cross Hospital, CA | EMERGENCY ROOM Shift Type: Variable Contract: Travel | RN | Tusar-test-001 Created On: Dec 24, 2015 By: Nelson R Submission from all agencies: 1 | December 01 2015 | Profile Selected for Onboard Ginger McClaren Comments Missing Docs | $ 70.0 | Important Message » 802 |
| Holy Cross Hospital, CA | IMAGING Shift Type: Variable Contract: Travel | CT | TRA-IMG-001 Created On: Dec 24, 2015 By: Joe Smith Submission from all agencies: 0 | January 01 2016 | | $ 122.0 | Propose 802 |
| Holy Cross Hospital, CA | CARDIOLOGY Shift Type: Day Contract: Travel | RN | TRAVEL-656 Created On: Mar 21, 2016 By: Joe Smith Submission from all agencies: 0 | April 30 2016 | | $ 75.0 | Propose |
| Heritage Oaks Hospital, CA | Dialysis Shift Type: Variable Contract: Day to Day | RN | D2D-DIAL-2015-JUL-003 Created On: Jul 22, 2015 By: Joe Smith Submission from all agencies: 1 | | Profile Selected for Onboard Jane Gale Comments Missing Docs | | Waiting for Compliance Verification |
| Holy Cross Hospital, CA | IMAGING Shift Type: Variable Contract: Day to Day | MRI | D2D-IMAGING-2016-MAR-006 Created On: Mar 14, 2016 By: Nelson R Submission from all agencies: 1 | | Profile Selected for Onboard Andy Jones Comments Missing Docs | $ 40.0 | Waiting for Compliance Verification |

Requisition: TRAVEL-656    Class: RN

| Class | First Name | Last Name | Compliance |
|---|---|---|---|
| RN | | | Any ▽  [Go] [Reset] |

902

April Chan
△ Non-Compliant    Rate [75.0]

Recent Proposal History

Holy Cross Hospital (Fremont, CA)
CRITICAL CARE    Onboard Completed on 02/26/2016

Previously completed onboard with Holy Cross Hospital, CA on 02/26/2016

[Propose]

902

Bridget Martinez
⊙ Compliant    Rate [75.0]

Recent Proposal History

Holy Cross Hospital (Fremont, CA)
CRITICAL CARE    Onboard Completed on 06/15/2015

Heritage Oaks Hospital (Fremont, CA)
Cardiology    Onboard Completed on 03/22/2016

Previously completed onboard with Holy Cross Hospital, CA on 06/15/2015

[Propose]

902

David Hawkins
△ Non-Compliant    Rate [75.0]

Recent Proposal History

Holy Cross Hospital (Fremont, CA)
CRITICAL CARE, LAB, EMERGENCY ROOM    Onboard Completed on 02/02/2016

Previously completed onboard with Holy Cross

[Back]

Requisitions 1000

| State | Facility | Sort by | |
|---|---|---|---|
| Select State | Select Facility | Class | Urgent Attention |
| | | Contract | Status |
| | | D2D & Travel | Open — Go |

| Facility | Department | Class | Requisition# | Start | Proposed | Rate | Action/Status |
|---|---|---|---|---|---|---|---|
| Holy Cross Hospital, CA | EMERGENCY ROOM Shift Type: Variable Contract: Travel | RN | Tusar-test-001 Created On: Dec 24, 2015 By: Nelson R Submission from all agencies: 1 | December 01 2015 | Profile Selected for Onboard — Ginger McClaren — Comments ♡ Missing Docs | $ 70.0 | Important Message » — 802 |
| Holy Cross Hospital, CA | IMAGING Shift Type: Variable Contract: Travel | CT | TRA-IMG-001 Created On: Dec 24, 2015 By: Joe Smith Submission from all agencies: 0 | January 01 2016 | 902 | $ 122.0 | Propose — 802 |
| Holy Cross Hospital, CA | CARDIOLOGY Shift Type: Day Contract: Travel | RN | TRAVEL-656 Created On: Mar 21, 2016 By: Joe Smith Submission from all agencies: 3 | April 30 2016 | Screening in Progress April Chan — Comments $75.0 Bridget Martinez — Comments $75.0 — 902 David Hawkins — Comments $75.0 | $ 75.0 | Propose |
| Heritage Oaks Hospital, CA | Dialysis Shift Type: Variable Contract: Day to Day | RN | D2D-DIAL-2015-JUL-003 Created On: Jul 22, 2015 By: Joe Smith Submission from all agencies: 1 | | Profile Selected for Onboard — 902 Jane Gale — Comments ♡ Missing Docs | | Waiting for Compliance Verification |
| Holy Cross Hospital, CA | IMAGING Shift Type: Variable | MRI | D2D-IMAGING-2016-MAR-006 Created On: Mar 14, 2016 | | Profile Selected for Onboard Andy Jones | $ 40.0 | Waiting for Compliance |

| Facility: Heritage Oaks Hospital, CA | | | | | | |
|---|---|---|---|---|---|---|
| Onboard | | | | View Onboard Status | | « |
| Department | Shift Type | Class | Agency | Name (click picture) | Requisition# | Interview | Approve |
| Dialysis | Variable | RN | Instastaff Nursing Registry | Jane Gale<br>🔒Screening Doc | D2D-DIAL-2015-JUL-003 | | Action |

Facility: Heritage Oaks Hospital, CA

Onboard  View Onboard Status  «

| Department | Shift Type | Class | Agency | Name (click picture) | Requisition# | Interview | Approve |
|---|---|---|---|---|---|---|---|
| Dialysis | Variable | RN | Instastaff Nursing Registry | | | | |

Close

Interview Date:

Send Interview Date

Approve    Deny

Approve only if interview and/or screening completed successfully

Figure 15

| Facility: Heritage Oaks Hospital, CA | | | | | | |
|---|---|---|---|---|---|---|
| Onboard | | | View Onboard Status | | | « |
| Department | Shift Type | Class | Agency | Name (click picture) | Requisition# | Interview | Approve |
| Dialysis | Variable | RN | Instastaff Nursing Registry | Jane Gale<br>Screening Doc | D2D-DIAL-2015-JUL-003 | April 20 2016 | Action |

Requisition

Requisition # D2D-DIAL-2015-JUL-003   Class RN   Department Dialysis
Shift Type                            Contract Day to Day   Facility Offered Rate Agency Rates and Terms Agency Bill Rate   Agency On Call Rate   Overtime Rate Policy   Doubletime Rate Policy Holiday Rate Policy                    Callback Rate Policy    Orientation Rate Policy Agency Float Policy                    Time Off Requested by Staff Approved By Facility
Facility Signature  Approved Date      Last Comment Agency
Agency Signature    Approved Date      Enter your comments here...

(1973 characters remaining)

[Bypass Offer] [Send Offer] [Deny] [Close]

Figure 18

| MSP: Bay Area MSP | | | | ◎ OK to Proceed ◎ Completed ◎ Waiting [«] |
|---|---|---|---|---|
| Onboard | | Sort by | Start Date - Earliest First | [?] |
| State | Facility | Agency Category | Agency | Requisition# | Status | [C] |
| Select State | Select Facility | ALL | Enter 3 characters | Enter 3 characters | IN PROGRESS | Contract |
| | | | | | | D2D & Travel [Go] |
| Facility | Department | Requisition# | Staff (click picture) | Start | Status | |
| Heritage Oaks Hospital, CA | Dialysis Shift Type: Variable Class: RN Contract: D2D | D2D-DIAL-2015-JUL-003 Received: Apr 01, 2016 ⚐ Missing Docs | [👤] Jane Gale Instastaff Nursing Registry [🔒 Screening Doc] | | [Screen > Intv > Offer > HR Audit🔒 > Hlth Audit🔒 > HR > Health > OR-Schd > OR-Vrfy > Final] [Next] [Swap] |

Figure 19

| HR Compliance Check | | | | | | |
|---|---|---|---|---|---|---|
| Facility | Department | Agency | Name (click picture) | Requisition# | Start | Ready for Review | Additional Comm |
| Heritage Oaks Hospital | Cardiac Cath Lab Shift Type: Variable Class: LVN | Instastaff Nursing Registry | John Smith [View and Approve] | TRA-HC-CCC-NOV25 ⚠ Missing Docs | 11/25/2015 | ⊗ | |
| Heritage Oaks Hospital | Dialysis Shift Type: Variable Class: RN | Instastaff Nursing Registry | Jane Gale [View and Approve] | D2D-DIAL-2015-JUL-003 ⚠ Missing Docs | | ⊗ | |

Figure 20

Health Compliance Review

Jane Gale
RN
Dialysis

Consolidated Document 🔒

Individual Document Review

| 10 Panel Drug 🔒 | Fit Test 🔒 | Hep B 🔒 | Influenza 🔒 | Mumps 🔒 |
| Last Updated: | Last Updated: | Last Updated: | Last Updated: | Last Updated: |
| Apr 04, 2016 | Apr 04, 2016 | Apr 04, 2016 | Apr 04, 2016 | Apr 04, 2016 |

| Physical Exam 🔒 | ReadySet ✎ | Rubella ✎ | Rubeola ✎ | TB Screening 🔒 |
| Last Updated: | | | | Last Updated: |
| Apr 04, 2016 | | | | Jul 09, 2013 |

| TDAP ✎ | Varicella ✎ |

— 2102

Checklist [Verify All]

| Hepatitis B  ⊘ ⊘ | Influenza  ⊘ ⊘ | Physical Exam  ⊘ ⊘ | TB Screening  ⊘ ⊘ |

[Approve] [Deny] [Send Message To Agency]

Jane Gale
RN
Dialysis

Health Compliance Review ✕

Consolidated Document

Individual Document Review

| Background Check | Certifications<br>Last Updated:<br>Jul 09, 2013 | EPLS/SAM | Education | Employment History |
| --- | --- | --- | --- | --- |
| HIPAA Form | Identification<br>Verification | License<br>Last Updated:<br>Mar 31, 2016 | Medi-Cal Suspension<br>and Ineligible<br>Provider Check | NSOPW |
| OFAC | OIG | References<br>Last Updated:<br>Jul 09, 2013 | Specialty | |

Checklist [Verify All]

| Background Check | National Sex<br>Offender Registry | OIG Search | Reference Check |
| --- | --- | --- | --- |
| Verified On:<br>Apr 01, 2016 | Verified On:<br>Apr 01, 2016 | Verified On:<br>Apr 01, 2016 | Verified On:<br>Apr 01, 2016 |

[Approve] [Deny] [Send Message To Agency]

MSP: Bay Area MSP  ◎ OK to Proceed  ◎ Completed  ◎ Waiting  [«]

Onboard

| State | Facility | Sort by | Agency Category | Requisition# | | Status | Contract |
|---|---|---|---|---|---|---|---|
| Select State | Select Facility | Start Date - Earliest First | ALL | Enter 3 characters | | IN PROGRESS | D2D & Travel |

[C] [?]  [Go]

| Facility | Department | Requisition# | Staff (click picture) | Start | Status | | |
|---|---|---|---|---|---|---|---|
| Holy Cross Hospital, CA | IMAGING Shift Type: Variable Class: MRI Contract: D2D | D2D-IMAGING-2016-MAR-006 Received: Mar 14, 2016 ♡ Missing Docs | [👤] Jane Gale Instastaff Nursing Registry [🔒 Screening Doc] Facility Offered  $ 40.00 Agency Proposed $ 40.00 | | Screen〉Intv〉Offer〉HR〉HR Audit🔒〉OR-Schd〉Final Hlth🔒〉Hlth Audit🔒〉OR-Vrfy [Next]  [Swap] | | |

MANAGED SERVICE PROVIDER SYSTEM FOR COLLABORATIVE HEALTHCARE CREDENTIALING, COMPLIANCE, AND SCHEDULING ACROSS SHARED SUPPLIERS

FIELD OF THE INVENTION

The invention relates to methods and a managed service provider (MSP) system for managing collaborative credentialing, compliance, and scheduling of contingent healthcare workers by multiple MSPs and healthcare facilities. More particularly, the invention relates to automatically fulfilling job requisitions, either travel or day-to-day workers, by employing services of suppliers available across the MSP system.

DISCUSSION OF THE RELATED ART

The traditional credentialing, compliance, and scheduling systems operate independently, and without an integrated process spanning the healthcare facility's stakeholders, the suppliers' stakeholders, and the healthcare workers. Such systems may be addressing the needs of a single healthcare facility in isolation without taking into account the overall demand, thereby creating an architecture that is built on simple data-exchange mechanism failing to see the overarching demand and availability in the context of the ecosystem. When workers are onboard one or more healthcare facilities, then the system for identifying their real-time availability is also not integrated. Lacking this level of cohesion and visibility, the current systems disenfranchise workers as well as process participants, which leads to inconsistent and incomplete credentialing and compliance, with added disadvantage of taking longer fill-cycles not in line with the hiring timeline and objectives of a healthcare facility.

Existing systems lack ability to create and manage shared supplier pool that can be dynamically configured within minutes to serve any group of healthcare facilities or MSPs. Systems also lack automated features to enable outsourcing of contingent staffing to an MSP, especially for healthcare systems that own several hospitals; additionally such systems lack the ability to create facility-specific configurations that vary from facility to facility. Accommodating each facility's unique circumstances and needs are therefore cumbersome, people intensive, and also lack a common communications platform with automated follow-ups, accountability, and life-cycle tracking of both the job order or the healthcare worker.

Existing systems also are not capable of automating process flows for engaging and alerting all stakeholders when posting, proposing, and onboard of a worker. This is because the worker, or candidate, profile has to flow through several layered steps that require collaboration between several stakeholders across both healthcare facility and suppliers. Typically the existing processes do not have a process fabric to seamlessly transition a worker profile across various stakeholders responsible for different organizations functions; these steps are job postings, responses, screening, interview scheduling, offer acceptance and contract compliance, credentialing, health record audits, HR acceptance, Health Services acceptance, facility and departmental orientation scheduling, and orientation delivery. With so many stakeholders, there is also a need to communicate all errors, omissions, and exceptions during this multitier process, and maintain its history.

With absence of a cohesive process across stakeholders and contributors, the ability to collect historical evidence for corroborating effectiveness of each individual step is absent. This is a serious drawback for harvesting lifecycle events for gaining operational intelligence that could be useful in optimization of core operations. Systems also lack real-time monitoring and alerting about non-compliance or non-employability, which are essential for patient safety and adhering to state regulations.

Existing systems also lack real-time scheduling features across multiple employers. The ecosystem of suppliers is not provided the tools to manage, monitor, and allocate workers across multiple employers. A major drawback of such systems is inability to take automated actions without manual intervention—for example, a shift that is announced automatically via VoIP (Voice-over-IP) or SMS (text messaging) would not be feasible in the absence of real-time calendaring; to assume that it is possible to do this without real-time information is to break all etiquette of communication and basically spam the suppliers and their workers with a deluge of irrelevant notifications about an opportunity that the worker is unable to fill.

SUMMARY OF THE INVENTION

Thus, a majority of healthcare facilities require contingent staff to ensure correct patient to healthcare worker ratio to avoid risks associated with being short staffed or overworked workers. Depending on the type of service a healthcare worker provides, however, regulatory organizations mandate who can provide direct service to patients. These regulatory requirements warrant credentialing, background, and health compliance verifications to ensure patient and healthcare worker safety, and avoid lawsuits when there is patient injury or death. It is often required to reproduce the compliance stance at a given point in history as proof of proper governance in hiring contingent workforce. In summary, a healthcare worker cannot provide services until the worker is properly whetted, oriented, and continuously tracked for any compliance violation.

For example, an expiring license, certification, or immunization would be considered out of compliance, and the healthcare worker has to replace the expiring document or prevented from providing patient care. Therefore, each such healthcare worker, after receiving clearance, has to be put into a qualified worker pool for a specific facility—only those workers who are in this pool can provide services at the said facility.

Real-time availability information is also important for creating multidimensional searchable view based on 5 key dimensions for informed on-demand shift provisioning—this dynamic view is constructed using department, job class, shift type, shift date, and worker availability and compliance. When this level of information is not easily available, it is impossible to create rich collaboration experience.

An MSP system for contingent staffing has 8 major components: (1) Ability to setup multiple MSP organizations, each servicing a number of healthcare facilities, which manage unique business relationships between healthcare facility and suppliers, (2) An ecosystem of suppliers and their healthcare workers shared across all MSPs. (3) A collaboration platform for all MSPs to coordinate with, and on-behalf-of, each healthcare facility serviced by MSP—ability to publish jobs across suppliers and receive automated candidate proposals, (4) An integrated workflow for various approvers/coordinators in the onboard of a candidate to include following steps—screening, interview scheduling, offer acceptance and contract compliance, credentialing, health record audits, HR acceptance, Health Services acceptance, facility and departmental orientation scheduling, and orientation delivery, (5) A tracking mechanism for all contingent staff for managing their employment lifecycle, history, and real-time compliance information, (6) Real-time virtual calendar of contract staff across multiple employers for day-to-day on-demand shift scheduling, (7) Multi-dimensional scheduling view to instantly schedule the most eligible candidate, and (8) Automated timecard generation, with mobile clock-in/clock-out.

The disclosed embodiments include a method for creating an MSP's Supplier (aka. Agency) ecosystem. The supplier ecosystem is shared with other MSPs. This effectively creates a marketplace between MSPs and suppliers. Each supplier can create its individual locations, and group such locations into national and regional hierarchies. Such groups belong to the same EIN (Employer Identification Number), which enables tracking of business operations at local, national, or regional level.

The suppliers are mapped to customers. Such customers are healthcare facilities created and uniquely configured. In some embodiments, the method creates departments specific to a healthcare facility. The method also creates job-classes mapped to specific departments. No other job classes can be used for onboarding healthcare workers if the job class has not been mapped to the department. The method also creates shift types unique to a facility and its departments, which represent start of shift, end of shift, total hours, and total permissible mealtime/breaks. All timecards and scheduling functions use shift types.

The method also creates unique credentialing steps later used for creating a dynamic checklist-menu during the compliance audit and HR acceptance processes. The method also creates unique health compliance steps later used for creating a dynamic checklist-menu during the compliance audit and health services acceptance processes. The method also creates performance evaluation criteria specific to a healthcare facility. The method also creates profile elements specific to a healthcare facility. The profile elements are mapped to specific job classes for dynamic profile-menu creation ensuring that unrelated profile elements remain hidden in the menu. The method also identifies dynamically those elements that require an accompanying document to be verified and approved during onboard.

Each agency has its administrators that create healthcare workers' profiles and a virtual calendar in the staff pool. An agency Administrator electronically submits all credential and health compliance documents. Profile elements that can be submitted include Licenses, Certificates, Identification, Education, Employment History, References, Skills/Specialty Assessment Worksheet, Confidentiality and HIPAA Form, Yearly Competency Assessment, Background Verification (EPLS/SAM, Medi-Cal License Suspension and Ineligible Provider Check, NSOPW, OIG, any additional background checks desired), Physical Exam Results, Medical Questionnaire, Immunizations Records (Mumps, Rubella, Rubeola, Varicella, TDAP, Hep B, Influenza), 10 Panel Drug Test, Drug and Alcohol Policy, FIT Test, TB Screening (PPD Skin Test, Quantiferon Test, Chest X-Ray), TB Questionnaire, and additional profile data as required by each healthcare facility. Because a healthcare worker may be employed by several agencies, each agency maintains a separate profile for healthcare worker as the profile is a portfolio of documents that the agency guarantees to be accurate, authentic, and validated by the submitting agency. Each profile entry has meta-data describing each document's validity and expiry period.

The Agency Administrator also manages the virtual calendar for each day-to-day worker. The virtual calendar is accessible by all agencies and healthcare facilities where the healthcare worker is employed. The calendar viewed by an agency, however, displays only those shifts that are contracted through the agency. The calendar viewed by a healthcare facility displays only those shifts that are pertaining to the facility. All other calendar entries are obfuscated.

The method creates compliance managers with responsibility for verifying all compliance related documents for specific set of healthcare facilities and its suppliers. The intersection of authorized healthcare facilities and authorized suppliers is the scope of access for the compliance manager.

The method also creates job orders, or requisitions, for electronic broadcast to suppliers. Broadcast of job orders can be limited to selected suppliers, can be sent to all suppliers in a single broadcast, or may be sent in batches on a deferred basis. Deferring allows responses from preferred vendors first.

The method is used by agency administrators to respond to a job order by proposing one or more candidates best suited for the job order. Job order is surfaced in the supplier's requisition queue, from where the Agency Administrator can select a specific job order and propose a viable candidate for the job by using an automated search for matching all qualified healthcare workers. The search shows all constraints in the context of the job order, compliance violations, and history of past and current proposals for each candidate along with their current onboard status with various healthcare facilities. This prevents over subscription of healthcare worker and avoids unnecessary withdrawals for an over-extended worker.

On proposing a candidate, the Agency Administrator can monitor the job order in the requisition queue as the candidate moves through various stages of the onboard process at the facility where proposed, therefore experiencing complete transparency in the entire onboard process. Additionally, the Agency Administrator receives alerts during onboard for additional documents, errors and omissions, interview date, offer acceptance, orientation dates, and alerts for cancelled or denied orders.

Responses for a job order are received by the MSP Staffing Manager. The responses may be from one or more suppliers, and each supplier may propose one or more healthcare workers. The MSP or facility-side response queue is called the Onboard Queue. Each entry in Onboard Queue represents one response, and each response follows a collaborative workflow, as disclosed below.

A method for an MSP Staffing Manager starts the first step of the collaborative onboard process by screening the candidate for fitment after which the candidate profile is forwarded to the interview step. While forwarding, the MSP Staffing Manager can provide the name of the interviewer, typically a department manager. If there are more candidates for a job order, then the additional candidates are held as backup. The Agency Administrator is informed when the candidate is selected for onboard, and all other candidates are moved in the backup queue for the agency from where such profiles may either be left as backup or recalled by the Agency Administrator for proposing to other healthcare facilities.

The candidate profile after successful screening is moved to the Department Manager, Interviewer, and Queue. Upon review of the screening document, the interviewer electronically sends an interview date to both the healthcare worker and the agency employing the healthcare worker. Upon completing the interview, a candidate is either approved or denied. An approval forwards the candidate to the next stage of onboard.

The candidate profile after successful interview is moved to the compliance manager queue. The compliance manager has two distinct queues. One for receiving all credentials required by HR and the other for receiving all health documents required by Health Services. A dynamic view is generated for the compliance manager, wherein all documents marked relevant for credentialing in the context of the healthcare facility are laid out in a tiled fashion in the top-half of the view with the ability to download and verify each document separately or as one consolidated document. For the bottom half, another dynamic view is generated, wherein both the credentialing checklist-menu and the health checklist-menu is laid out in a tiled fashion in the bottom-half of the compliance manager view with ability to check-mark each step as verified. If the profile could not be verified due to omission, negligence, illegible documents, or expired documents, then an automated notification with relevant comments are sent to the Agency Administrator for remedial action, and the profile is marked in the Compliance Manager Queue as 'Agency Alerted'. In response to this alert, the Agency Administrator certifies taking remedial action to address all deficiencies, which in turn marks the profile in the compliance manager queue as 'Agency Responded' and shows the response received.

The candidate profile after checklist approval is moved to the HR Administrator and Health Services Administrator queues. Both HR and Health Services personnel verify and approve each candidate in a manner similar to the compliance manager using identical user interface and software logic, except that both HR and Health Services personnel may also revert a profile back to the compliance manager for further investigation.

The candidate profile after checklist approval is moved to the orientation scheduling step in the collaborative workflow. The orientation schedule is copied from a modifiable template, updated for the current requisition, and sent to both the healthcare worker and its Agency Administrator. The orientation schedule consists of dates, time, and reporting instructions. Soon after orientation is completed, the candidate is verified for successfully completing all the assigned orientation steps.

The candidate profile after Orientation checklist approval is moved to the final step in the collaborative workflow where the contract's start and end date may be altered and alerted to both the agency and the candidate. The conclusion of this final step stages the candidate in the facility's staff pool for tracking the contract history, real-time compliance, performance evaluation, and several other attributes of a healthcare worker with respect to his/her employment with the facility. On conclusion of the contract period as specified in the job order, if this candidate is resubmitted for a new job order in the future, then the entire onboard process for this healthcare worker may be either repeated, bypassed, or certain steps may be selectively bypassed depending on the length of time that the worker has not worked at the same facility or in the same department.

A method is used by the MSP Staffing Manager for searching, inviting, and confirming shifts from available compliant-healthcare workers using a 5 dimensional drill-down approach to include Departments, Job Class, Shift Types, Date, and time intersection, and displaying the 5 dimensional data for multi-department, multi-class, multi-shift type, multi-date, and multi-worker selection. This view is derived from existing shift allocations attached to job orders for the healthcare facility and virtual calendars of healthcare workers across the entire supplier ecosystem, wherein each shift has a backing timecard accessible by healthcare worker using mobile device.

An additional method is used by the MSP Staffing Manager for searching, inviting, and confirming shifts from available compliant-healthcare workers by constructing date specific vertical swim-lanes grouped by department. This view is derived from the virtual calendars of healthcare workers across the entire supplier ecosystem. Each shift has a backing timecard accessible by healthcare worker using mobile device.

An additional method is used by the MSP Staffing Manager for searching, inviting, and confirming shifts from available compliant-healthcare workers by constructing date specific horizontal swim-lanes by available staff. This view is used for distributing a multiday order between candidates by mix-and-match, with automated VoIP based interaction to confirm multiday availability. This view is derived from the virtual calendars of healthcare workers across the entire supplier ecosystem. Each shift has a backing timecard accessible by healthcare worker using mobile device.

BRIEF DESCRIPTION OF THE DRAWINGS

The accompanying drawings are included to provide further understanding of the invention and constitute a part of the specification. The drawings listed below illustrate embodiments of the invention and, together with the description, serve to explain the principles of the invention, as disclosed by the claims and their equivalents.

FIG. 7 illustrates an example job-order queue for an MSP according to the disclosed embodiments.

FIG. 8 illustrates an example job-order queue for a supplier according to the disclosed embodiments.

FIG. 9 illustrates an example search and match screen that shows all eligible candidates to a supplier according to the disclosed embodiments.

FIG. 10 illustrates an example screen of a supplier submitting one or more candidates according to the disclosed embodiments.

FIG. 13 illustrates a screen of the MSP of the interview queue according to the disclosed embodiments.

FIG. 14 illustrates the screen of the queue for an interviewer according to the disclosed embodiments.

FIG. 15 illustrates the interviewer date selection screen according to the disclosed embodiments.

FIG. 16 illustrates the interview date display according to the disclosed embodiments.

FIG. 17 illustrates the screen for the MSP view of the offer queue according to the disclosed embodiments.

FIG. 18 illustrates a screen showing offer negotiation and confirmation according to the disclosed embodiments.

FIG. 19 illustrates the screen of the MSP view of a compliance manager queue according to the disclosed embodiments.

FIG. 20 illustrates a screen showing the compliance manager queue according to the disclosed embodiments.

FIG. 21 illustrates a screen for individual health document review and approval according to the disclosed embodiments.

FIG. 22 illustrates a screen for individual HR document review and approval according to the disclosed embodiments.

FIG. 24 illustrates a screen showing the MSP Staffing Manager creating an orientation schedule according to the disclosed embodiments.

FIG. 26 illustrates the screen for the MSP view of completion of orientation according to the disclosed embodiments.

FIG. 30 illustrates a screen of selection criteria for creation of a 3-dimensional view according to the disclosed embodiments.

FIG. 33 illustrates a search screen for VoIP multiday scheduling according to the disclosed embodiments.

FIG. 35 illustrates the MSP view screen showing the healthcare worker in the invited queue according to the disclosed embodiments.

FIG. 37 illustrates the supplier view screen when the healthcare worker is moved to the confirmed queue on accepting the shift(s) according to the disclosed embodiments.

DETAILED DESCRIPTION OF THE PREFERRED EMBODIMENTS

Figure 1:
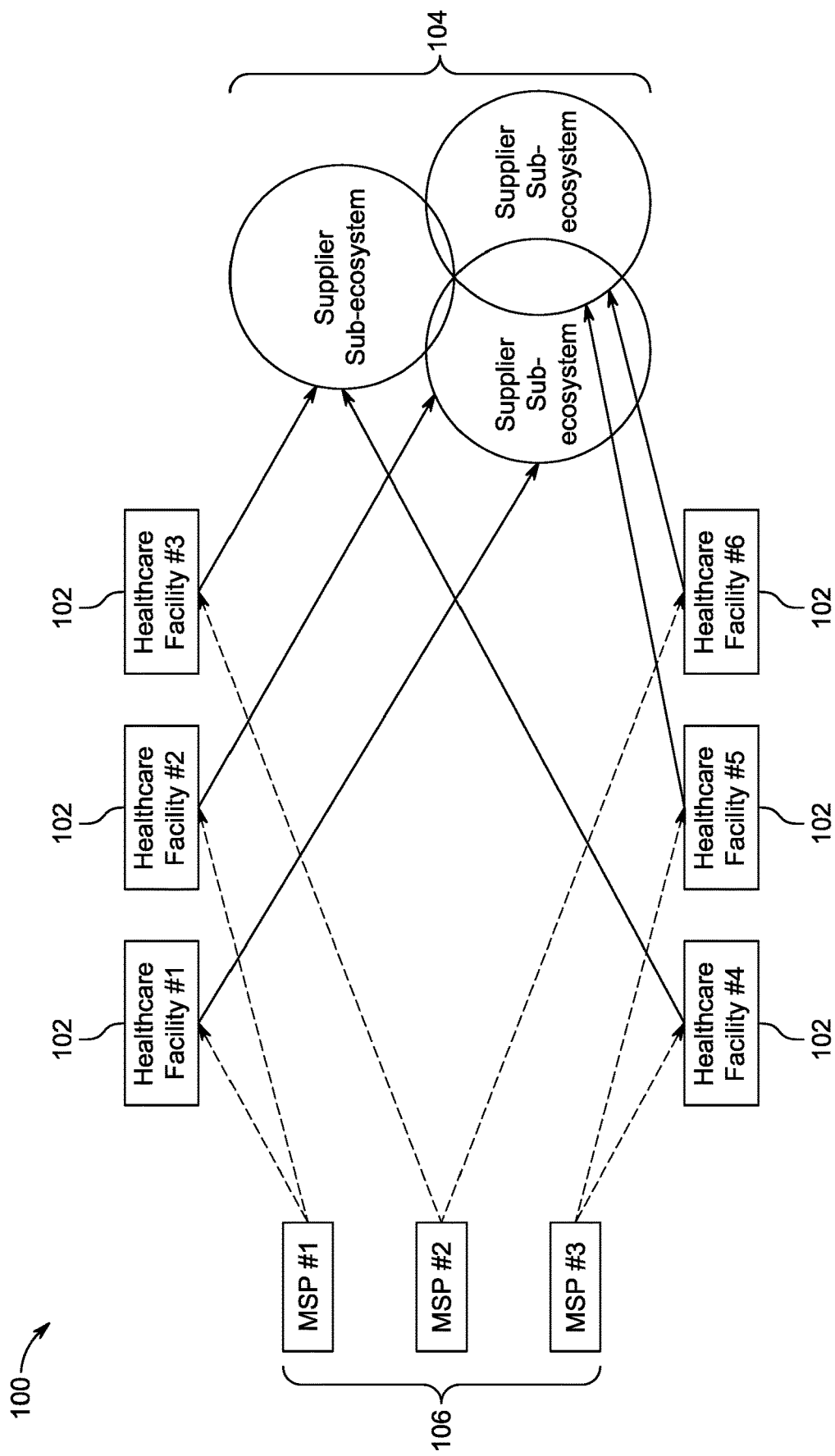
FIG. 1 illustrates an MSP ecosystem according to the disclosed embodiments.

Aspects of the invention are disclosed in the accompanying description. Alternate embodiments of the present invention and their equivalents are devised without parting from the spirit or scope of the present invention. It should be noted that like elements disclosed below are indicated by like reference numbers in the drawings.

The process of ensuring healthcare worker compliance and credentialing is fraught with inefficiencies, errors, omissions, visibility, and poor tracking. This is because of the fact that there are many participants in the process of identifying, screening, and assigning shifts to healthcare worker. The complexity of interactions is explained below.

FIG. 1 shows the MSP ecosystem 100 according to the disclosed embodiments. First tier of complexity arises in creating a collaborative ecosystem wherein a large number of healthcare facilities 102 use a set of suppliers 104. Different healthcare facilities 102 use the same subset of a larger ecosystem. The relationships between such an expansive ecosystem has to be mapped to ensure that a new facility can be up and running with a supplier ecosystem in a few hours rather than months of RFPs, contract negotiations, etc. By the same token, a supplier should be able to plug itself into this ecosystem and start supplying in matter of hours to a preexisting customer base. Another dimension of complexity is when an MSP 106 provides total outsourcing solution for staffing operations that includes contract management, compliance management, day-to-day staffing, invoicing, and other staffing and support services.

Figure 2:
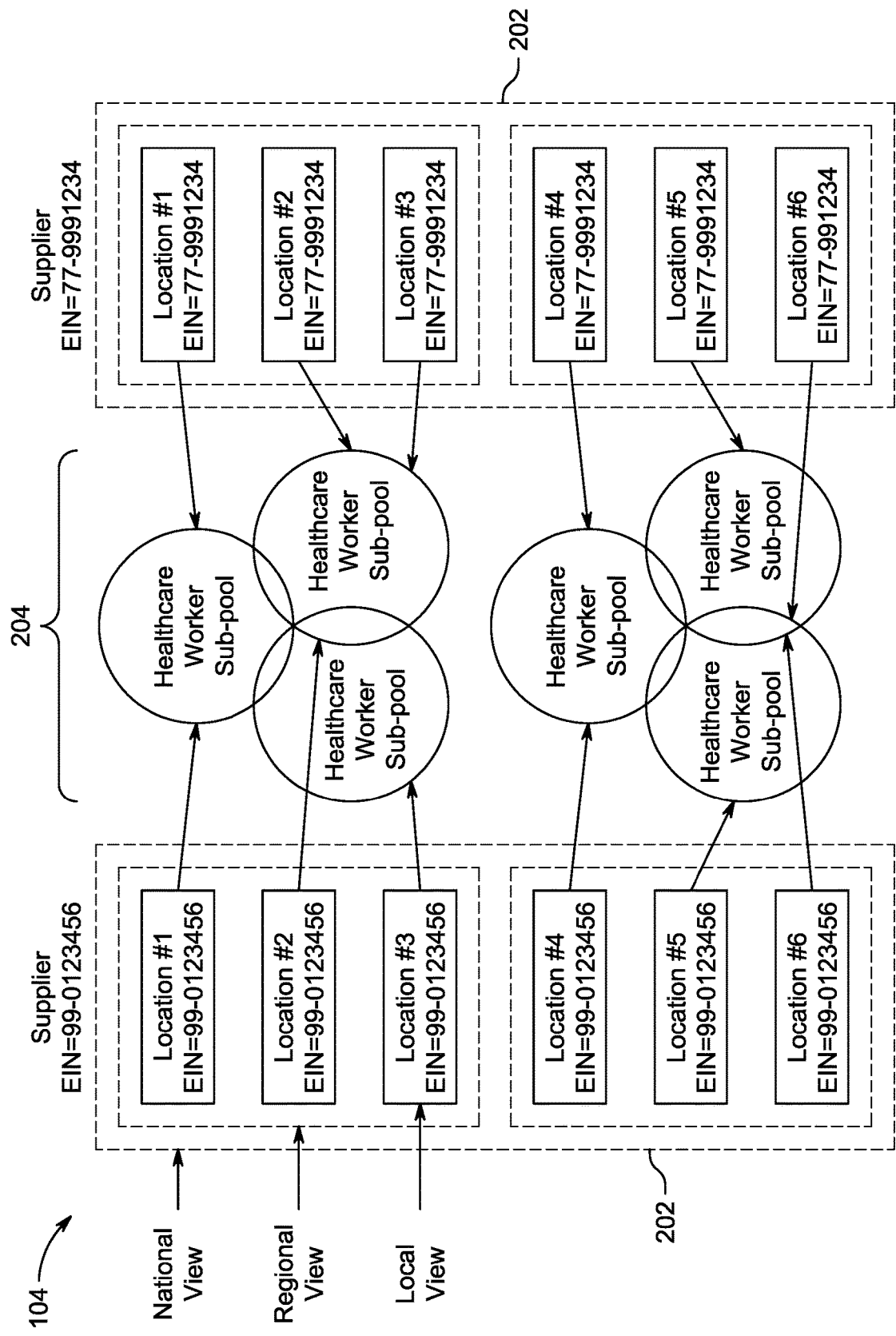
FIG. 2 illustrates a supplier ecosystem according to the disclosed embodiments.

FIG. 2 shows a supplier ecosystem 104 according to the disclosed embodiments. Whether a supplier 202 is a single-location shop or a multi-location national supplier, the suppliers essentially are competing for available healthcare workers 204 in the market, and essentially are hiring workers that can be working at other suppliers. In this shared ecosystem 104, there is constant battle to get a job order to ensure that the supplier can provide contingent healthcare worker with continued income or risk losing the worker to a competitor. The opportunistic aspect of the worker pool creates another level of complexity. Each employer has to maintain its own worker profile and ensure its accuracy and validity. By the same token, the MSP platform 100 prevents collisions of submissions of the same healthcare worker through multiple suppliers at the same facility. Through a fairness system, the healthcare worker acceptance by a healthcare facility from a specific supplier essentially prevents other suppliers from submitting the same candidate.

Complexity of Electronic Record Keeping, Credentialing, and Compliance

Figure 3:
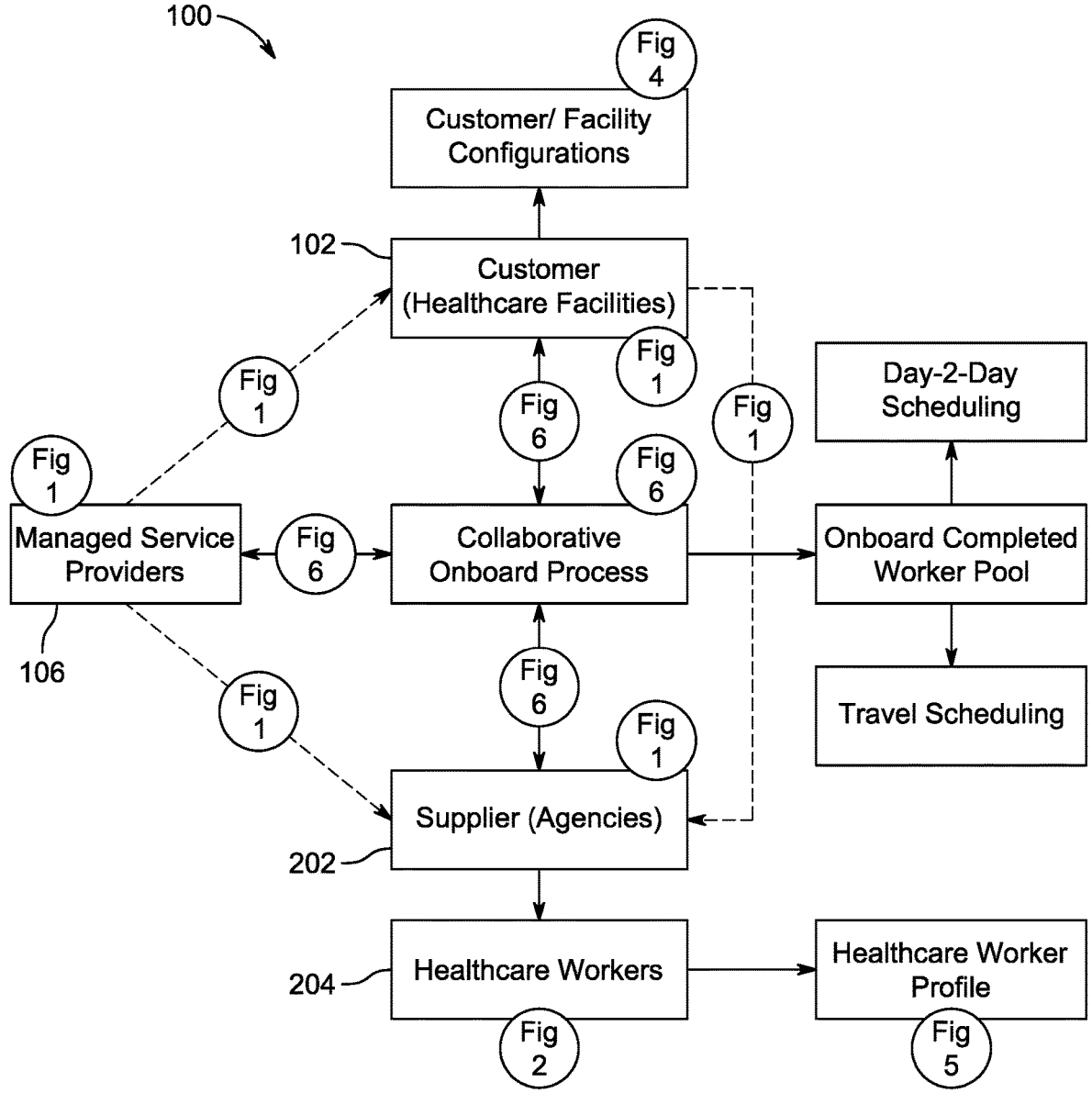
FIG. 3 illustrates the MSP structure and key processes according to the disclosed embodiments.

The credentialing and compliance repertoire is very extensive. A subset of this profile is shown in FIG. 3, and the requirements could vary from facility to facility. Where applicable, the element within the profile will have a corresponding expiry date, which has to be tracked continuously and various stakeholder alerted ahead of time before such documents expire. When a supplier 202 is working with large number of healthcare facilities 102, or when the healthcare facility is working with a large number of suppliers then it becomes difficult to track this information flow, including the verification required for both correctly submitted documents, or new versions of document requested in case of expiring documents. Additionally, a repository of current documents and historical documents has to be maintained for audit purpose, and should be available on demand. Given the high volume of contingent workers going through larger healthcare facilities every year, the complexity of submitting, reviewing, approving, replacing, and reporting on such documents without a management system means error prone and inefficient process fraught with risks. The MSP system 100 has taken this process from several weeks and compressed it to just few hours as evidenced by real world benchmarking.

Complexity in Chain-of-Approval and Accountability

Figure 6:
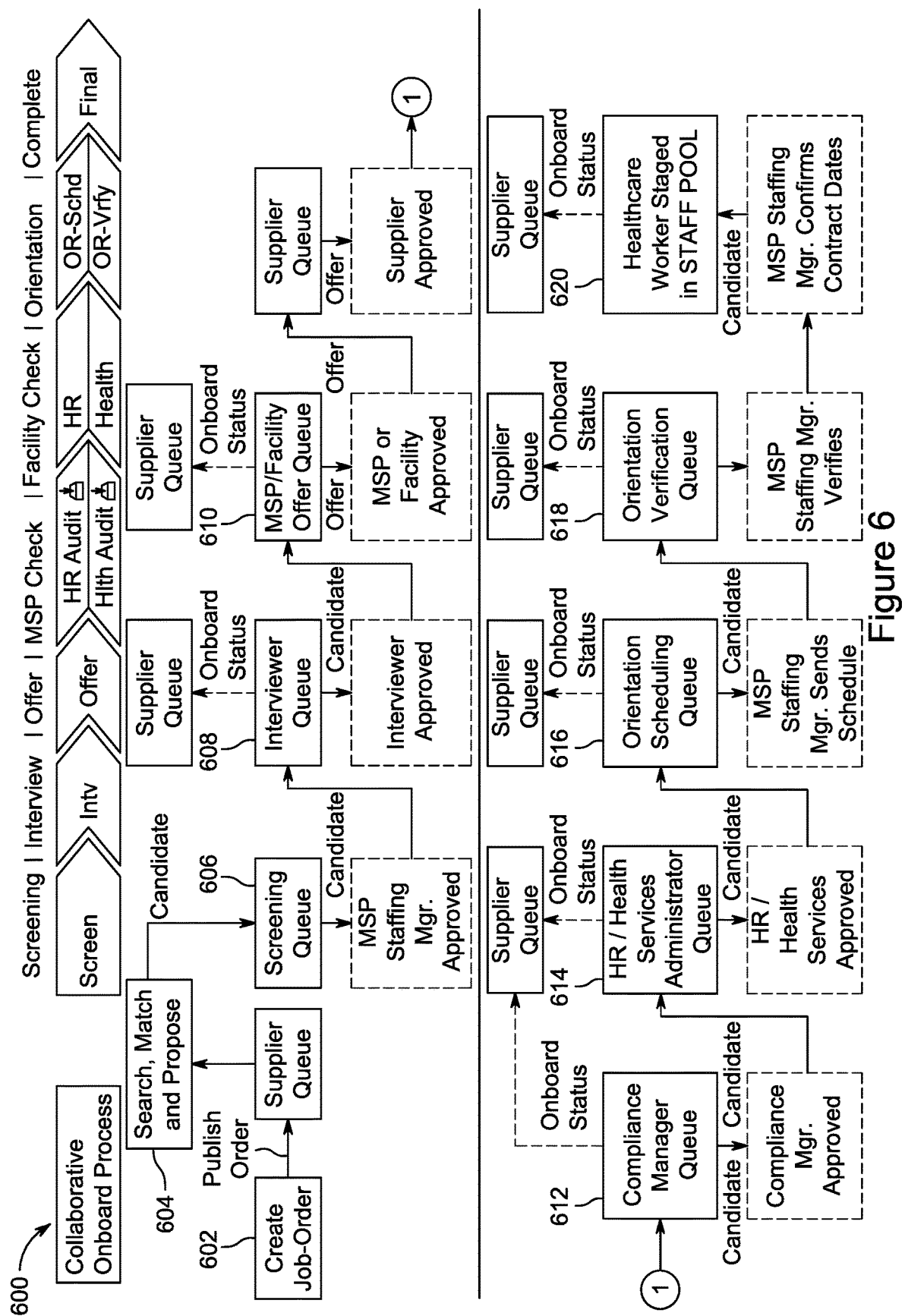
FIG. 6 illustrates a flow diagram for a collaborative process according to the disclosed embodiments.

FIG. 6 in the section MSP Platform for Contingent Staffing below shows the entire process from job-order creation to completion of all onboard steps that finally qualifies a worker for shift assignments. The numerous suppliers that may bid for a job-order, propose one or more candidates, and the various stakeholders that would screen, interview, audit, approve/deny, and orient a candidate requires an integrated process to include all participating entities, including the worker. In such a process, the documents and information has to move from one stakeholder to another in an orderly fashion while maintaining the integrity and sanctity of the documents, notes captured by each process contributor, and keeping historical evidence of the entire process for forensics and reporting. One key aspect of the forensics is optimization of process and analyzing where the process bottlenecks exist, and which group of contributors is responsible for slowing the process, and may require more resources or training.

Complexity in Deriving Business Metrics for Business and Process Optimization

Contingent staffing spend is attributed to various cost centers in healthcare facilities. C-suite requires visual representation to assess the impact of contingent staffing on organizations performance measure from various metrics, chiefly cost, time-to-onboard, job-order turnaround, supplier performance, risk, patient-to-staff ratio, shortage of specific skill set, patient satisfaction, etc. These metrics derived by mining the data provide insight into various parameters that could be adjusted to improve quality, cost, and risks.

Complexity of Scheduling On-Demand Day-to-Day Staff

The most difficult situation arises when Day-to-Day shifts are required to be filled. Without a virtual calendar capturing all assignments of a staff across multiple employers, vacations, non-availability, and other types of schedule blocks, there is no visibility into the worker's availability. The only option in this case is to broadcast the shifts across a wide network, which disincentivizes the suppliers, as the effort required in contacting, confirming, reciprocating back with an available resource could be met with a rejection when there are several respondents. The market is therefore disdainful about participating in such random markets, which causes serious availability issues for healthcare facilities, as too few suppliers want to play in this market.

FIG. 3 shows the MSP structure and key processes according to the disclosed embodiments. MSP platform 100 may be used for contingent staffing. The MSP solution discussed here addresses all of the above-mentioned complexities by creating a electronic marketplace for onboard of both healthcare facilities (the customers) and staffing agencies (the suppliers), with ability to form self-contained networks between healthcare facilities and suppliers. An MSP platform 100 with responsibility of outsourced contingent staffing operations could create its own customer ecosystem within this platform to service and manage. A healthcare facility 102 which does not need the services of a MSP, can creates itself as an MSP and manage its group of hospitals and its suppliers. A supplier 202 can create a multi-location presence by creating all of their independent locations and then aggregating them using the unique EIN # for its organization. All of these different hierarchies provide ability for each entity to manage their business operations at the MSP level, facility level, or supplier level. Each entity can also self-onboard their ecosystem, thereby using the MSP platform 100 as a true platform for enabling commerce between participating entities as further elaborated with the help of the FIG. 3 below.

Figure 4:
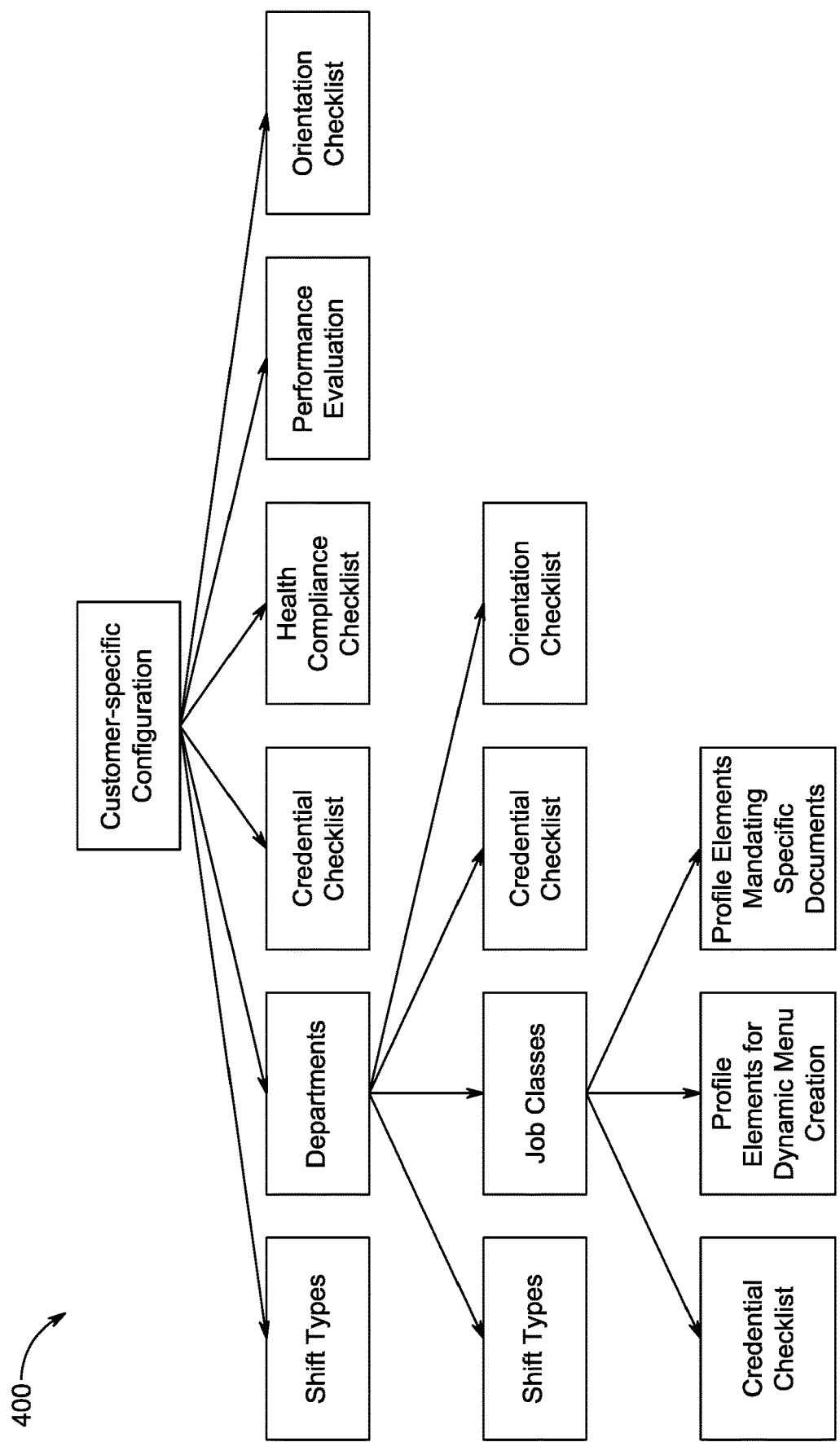
FIG. 4 illustrates sample elements of a healthcare facility custom configuration according to the disclosed embodiments.
Figure 5:
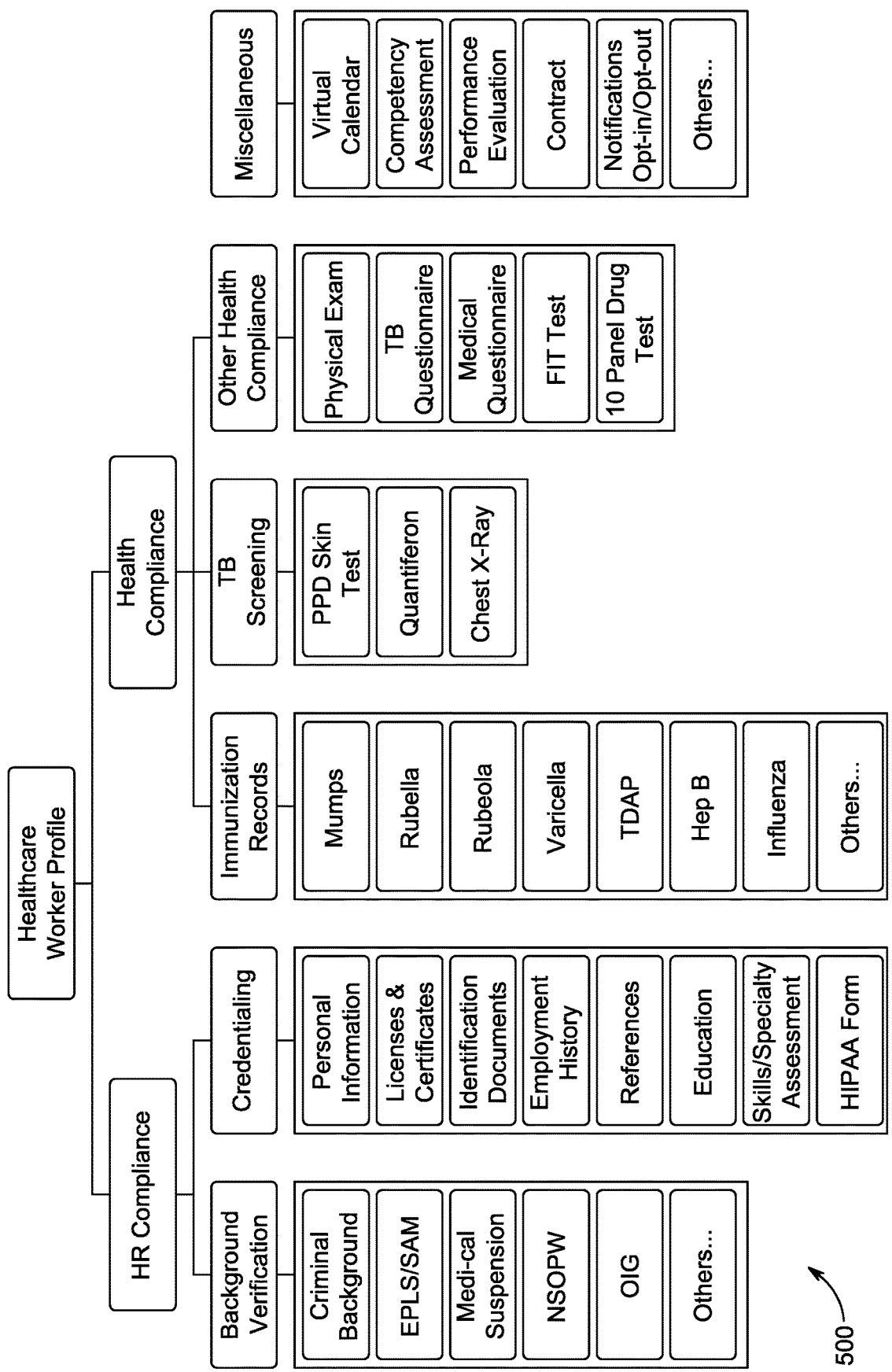
FIG. 5 illustrates a sample profile for verification of credentialing and compliance documents according to the disclosed embodiments.

FIG. 3 illustrates key principles in MSP platform 100 architecture. The concepts disclosed therein are elaborated upon in FIGS. 1, 2, 4, 5, and 6. FIGS. 5 and 6 are disclosed in greater detail below.

MSP platform 100 includes the following key elements. First is the ability to create and configure MSPs 106 that receive the privilege of establishing their presence in the platform and use the services of the platform to serve healthcare facilities 102 by managing their contingent staffing operations. A healthcare facility 102 can be its own MSP, or a group of facility (example: a hospital system) can also create its own MSP or use services of an outside MSP entity.

Another ability is one by the MSP 106 to create and configure customers. Each customer is uniquely configurable so as have services vary in behavior dynamically at run-time without requiring programmatic changes. These customizable configurations 400 are shown in FIG. 4, which depicts sample elements of a healthcare facility 102 custom setup.

The MSP 106 creates and configures suppliers 202 as either independent location, or creates a multi-location supplier. Each such supplier is identified as either providing TRAVEL healthcare workers (meaning 1-14 weeks of contract) or providing DAY-TO-DAY healthcare workers (meaning On-Demand as the need arises, contract period is open ended), or providing both types of contingent workforce. Suppliers 202 can add themselves and expand their locations within the MSP platform 100 through self-registration. All suppliers 202 are visible to all MSPs 106 and to all healthcare facilities 102 even when a specific MSP has added a particular supplier to the ecosystem.

Each supplier location has the ability to add workers to its pool that will be then proposed to various job orders originating from the healthcare facilities. For each worker 204, the supplier 202 has to supply credentialing and compliance information as shown in FIG. 5, which depicts a healthcare worker profile 500.

MSPs 106 have the ability to do mapping between the hospitals and the supplier locations that service them. This restricts the number of suppliers based on the preferred vendor list approved by the healthcare facility.

At its core the MSP platform 100 has a powerful Collaborative Onboard Platform that allows MSP 106 or its constituent facilities to request for healthcare workers 204 with either TRAVEL or DAY-TO-DAY contracts. This Onboard Platform brokers all requests for healthcare workers using Job-Orders, and then engages all stakeholders who have to review and approve the candidates. Additionally the platform 100 prevents collision between suppliers that propose the same candidate to a facility. The platform 100 also prevents suppliers from overcommitting the worker by alerting the supplier on overlapping contracts and shifts.

All healthcare workers 204 that have been qualified and successfully added to a facility's pool are then available to be scheduled for long term or short-term assignments based on their designation as either TRAVEL or DAY-TO-DAY workers. The DAY-TO-DAY scheduling platform is at the core of MSP platform 100 for providing automated scheduling using multidimensional day-to-day scheduling wherein hundreds of shifts for the entire healthcare facility 102 can be scheduled in minutes by consulting the virtual calendar for each qualified worker that completed onboard for day-to-day contracts.

MSP platform 100 encapsulates and hides the complexity involved in publishing and fulfilling a job order for a healthcare worker 204 to a large supplier network of ecosystems 104. MSP platform 100 also receives and processes the candidates through a complex onboard process. As disclosed in FIG. 6, there may be 8 steps involved in the end-to-end process, each involving a pipeline of 8 queues through which a healthcare worker 204 profile should pass through before successfully meeting all the criteria for qualification and ready to deliver patient care. Each queue identified below may be managed by different entities. Responsibilities for each queue depend on how a MSP 106 or a healthcare facility 102 has distributed them.

As shown in collaborative onboard process flow bar 600, the process may be broken into 7 segments. These segments may be screening, interview, offer, MSP check, facility check, orientation and completion. After going through these segments, then a healthcare worker is ready for assignment to shifts within MSP platform 100.

Once a job-order is created to onboard a new healthcare worker in step 602, it is staged both in the MSP's Job-Order Queue and Supplier's Job-Order Queue from where the supplier 202 will propose eligible candidates along with a screening document. These actions occur in the search, match, and propose process embodied in step 604.

The submitted candidates will be staged in the Screening Queue 606 where the MSP or facility position controller will review the screening document and approve or deny a proposed candidate. If more than one candidate is offered for a job-order, then when a candidate is selected, other candidate profiles are marked as backup profiles and put into holding pattern for reconsideration should the original candidate chosen for onboard is no longer available or fails to meet the onboard requirements. On successful screening, the candidate is moved to the next stage of the process, which is the interview segment of process 600. A list of interviewers or department managers are listed for their authorized departments, and the candidate is moved into the Interviewer Queue 608. Position-Controller can post additional information while forwarding the candidate profile to the Interview Queue.

The interviewer will electronically send a specific interview date. Email, VoIP, and text are available channels. The interviewer completes the interview, posts the results of the interview, and forwards the candidate profile to the MSP/Facility Offer Queue 610.

Offer Queue 610 includes a two-step process. First the offer is signed and sent by the facility officer with signing authority. The supplier acknowledges the offer by counter signing it. The offer step provides a chat session for facilitating negotiations and additional terms. On completion of the Offer segment of process 600, the candidate profile is forwarded for credentialing and compliance verification to the Compliance Manager's Audit Queue 612.

In the audit segment of process 600, the compliance manager will verify all submitted documents for accuracy, errors, omissions, and validity, before approving the candidate profile to be sent to the facility HR and Health teams for final review and approval. The audit segment is made up of two steps. One step is for documents relevant to the facility's HR team, and the other for the facility's Health Services team. On approval of all documents in the audit steps, the profile is moved to two queues, HR and Health Queues 614.

In the HR and Health Queues 614, the facility's HR and Health Services team will do one final review to ensure that all facility related credentialing and health compliance rules are observed. Any anomalies are brought to the attention of Compliance Manager by reverting the profile back to Compliance Manager Queue 612. When the profile meets all the facility requirements then it is sent to the Orientation Queue 616.

In the Orientation Queue 616, the education services and/or the MSP Staffing Admin will create an orientation schedule from a pre-existing orientation template and send it to the suppler and the candidate. At this time, the profile is moved to Orientation Verification Queue 618. While in the orientation queue 616, the results of the orientation are posted in the MSP platform 100 for each orientation segment of process 600 completed, and when all steps are marked as done then the profile is moved to the final segment.

In the final segment of process 600, the profile is marked as completed. Any notes that need to be captured about the candidate are also posted, and the candidate is then moved to the qualified staff pool 620 for the facility along with the complete history of onboard and related notes from all the assessors.

FIG. 7 shows the job order queue 700 for an MSP 106. The MSP 106 creates a job order by clicking create requisition 702 in the screen shown in FIG. 7. The screen for job order queue 700 illustrates where all newly created orders are staged.

FIG. 8 shows a job order queue 800 for a supplier 202. Each broadcasted job order is visible to one or more suppliers 202 as shown in the figure. A supplier 202 can respond to the requisition, or job order, by clicking propose button 802, which initiates the searching and matching algorithm. The action/status column 804 shows the progress of a profile through the onboard process along with an indicator showing all documents required for credentialing and compliance that are still pending for the candidate. When MSP 106 selects candidates from the list proposed by the supplier(s) 202, the supplier 202 is able to see which healthcare worker 204 was selected by MSP 106.

FIG. 9 illustrates an example search and match screen 900 that shows all eligible candidates to a supplier 202 according to the disclosed embodiments. The search and match function shows all eligible candidates 902 for a specific job class. This is illustrated below. Also shown is the onboard status history to prevent over subscription for the candidate 902. A previously submitted candidate 902, or one that is already part of another job order, is prevented from resubmission. Compliance alerts are also shown in the context of healthcare-specific rules. FIG. 10 illustrates an example screen 1000 of a supplier 202 submitting one or more candidates 902 according to the disclosed embodiments.

Figure 11:
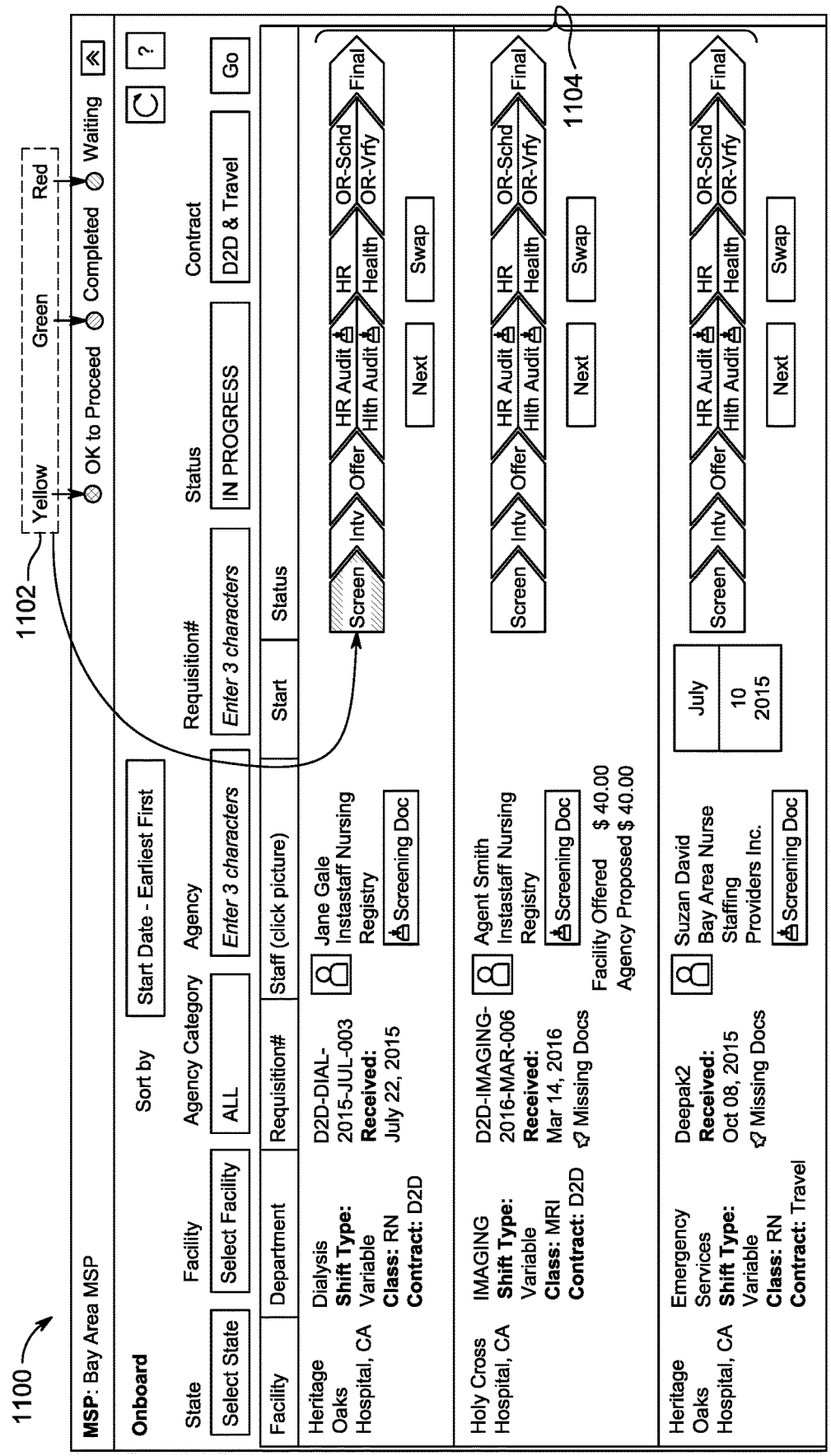
FIG. 11 illustrates a MSP view of the screening queue according to the disclosed embodiments.

Actions pertaining screening queue 606 are disclosed. FIG. 11 illustrates a MSP screen 1100 of the screening queue 606 according to the disclosed embodiments. Proposed healthcare workers 902 are shown in screening queue 606. The screening document submitted for candidate 902 is reviewed for fulfilling the job, as shown in FIG. 11. A colored indicator 1102 may be used, wherein the colors yellow, green, and red are used to highlight the status of the different candidates 902 shown in screen 1100. Further, screen 1100 may show the status of each candidate using process bars 1104, which resemble process 600. Various types of information may be shown in screen 1104.

Figure 12:
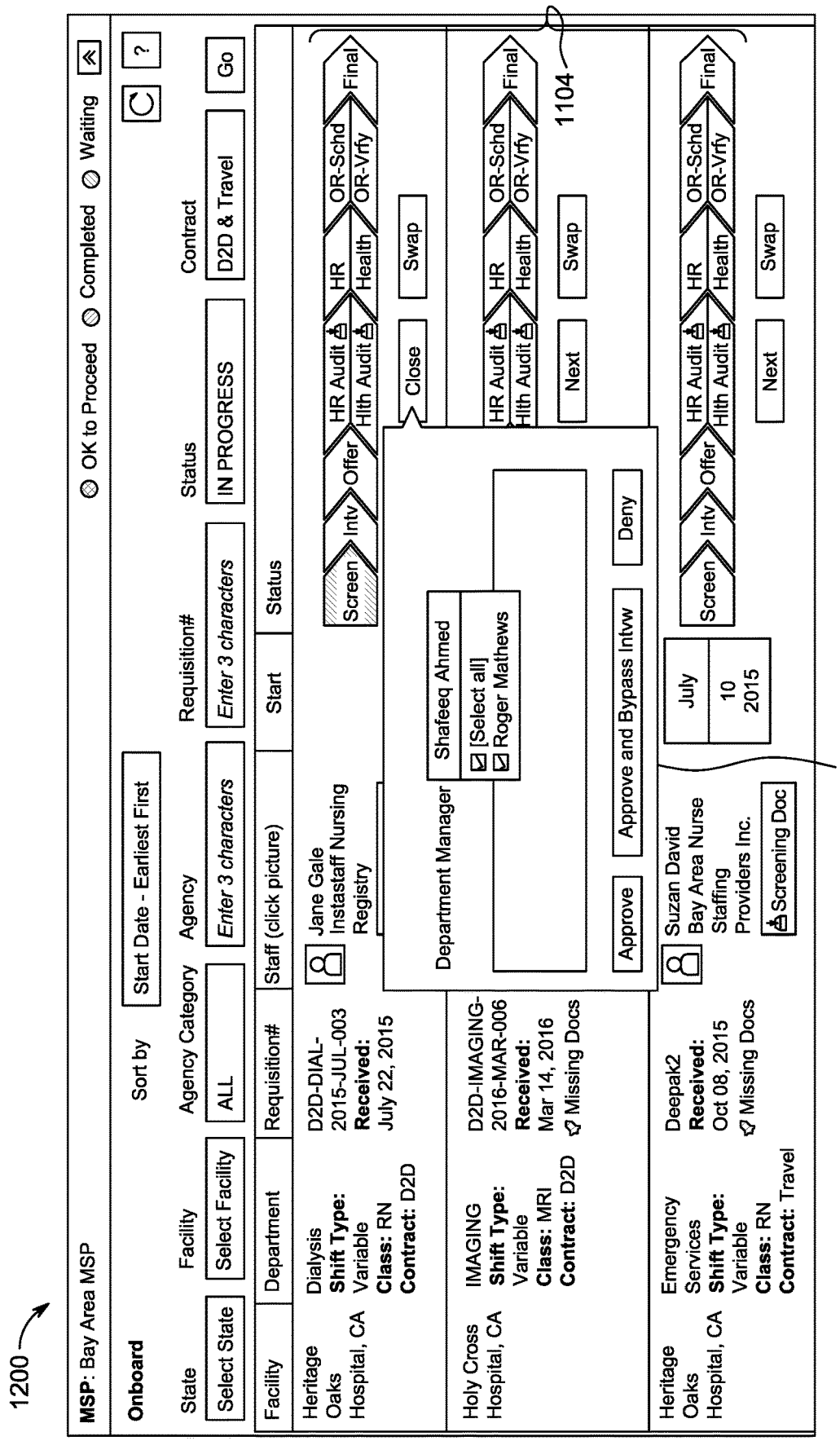
FIG. 12 illustrates the MSP's Position Control forwarding a candidate to an interview queue according to the disclosed embodiments.

FIG. 12 illustrates a screen 1200 showing the MSP's Position-Control forwarding a candidate 902 to an interview queue according to the disclosed embodiments. When the screening process is complete, a candidate 902 can be rejected or forwarded to interviewer queue 608. A drop down menu 1202 may be used to select how the candidate is to be treated.

Figure 13:
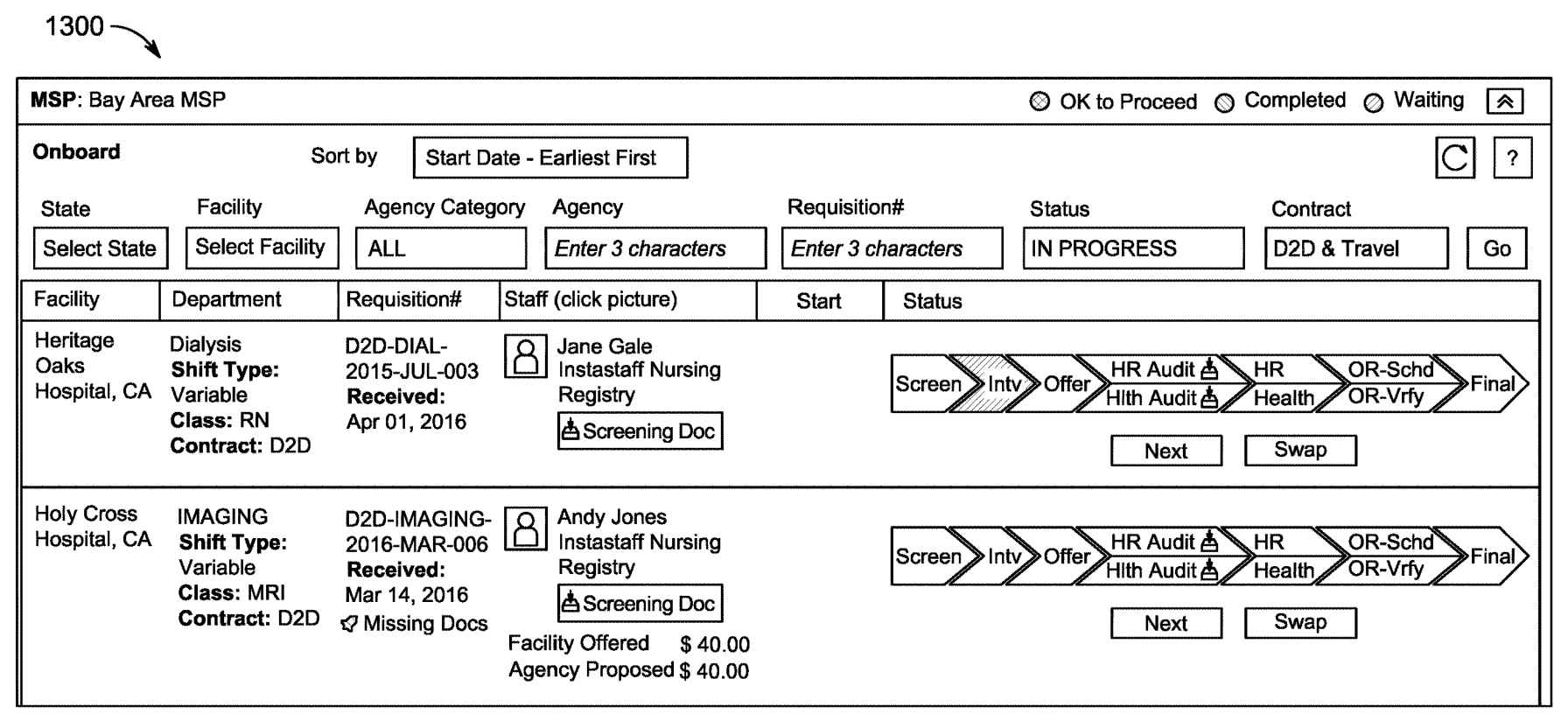

FIG. 13 illustrates a screen 1300 of the view for MSP 106 of the interviewer queue 608 according to the disclosed embodiments. FIG. 14 illustrates the screen 1400 of the queue 608 for an interviewer according to the disclosed embodiments. An interviewer/department manager logs into his/her portal and is presented with screen 1400 of interview queue 608. FIG. 15 illustrates the interviewer date selection screen 1500 according to the disclosed embodiments. The interviewer selects a candidate 902 for scheduling an interview as shown in the figure. When an interview date is selected, the system 100 automatically sends an email or text notification to both the healthcare worker 204 and supplier 202. This may be shown in FIG. 16 by interview date display screen 1600.

Figure 17:
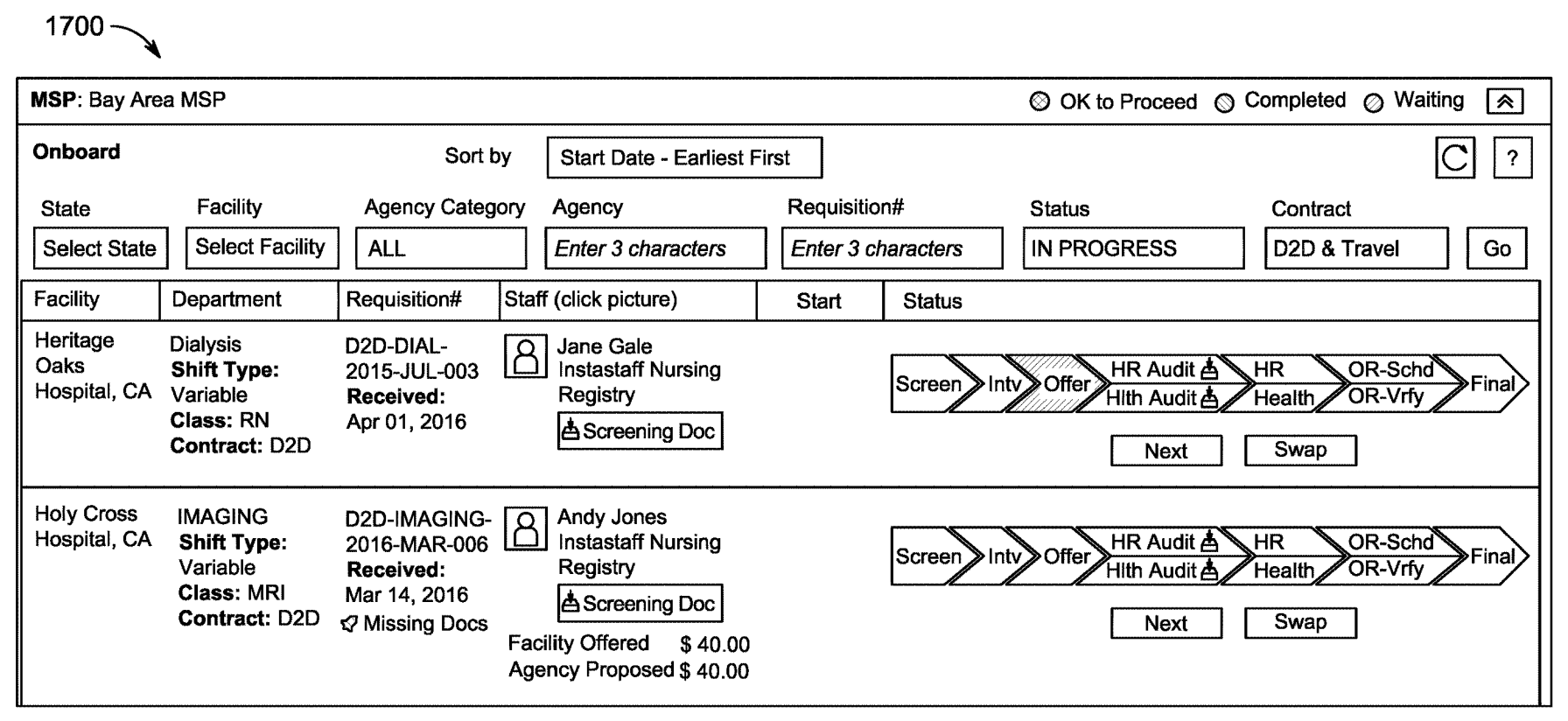

Upon a successful interview, the healthcare worker profile is approved, which automatically forwards the profile to the offer segment of process 600. FIG. 17 illustrates the screen 1700 for the MSP view of the offer queue 610 according to the disclosed embodiments. FIG. 18 illustrates a screen 1800 showing offer negotiation and confirmation according to the disclosed embodiments. In the offer segment, the engagement period and all the various terms of engagement are shown. This requires signing by both the MSP 106, or healthcare facility 102, and the supplier 202. There may be a back-and-forth negotiation, which are depicted in the chat bubble, and recorded for future audit.

Once the offer segment is completed, the profile is transferred to the compliance manager queue 612 for credentialing and health compliance. This may be an optional compliance step, which is only shown if the option is turned on. This feature dynamically inserts HR Audit and Health Audit (Health) steps. These are the credentialing and health compliance steps performed by an intervening compliance manager and available on demand.

FIG. 19 illustrates the screen 1900 of the MSP view of a compliance manager queue 612 according to the disclosed embodiments. FIG. 20 illustrates a screen 2000 showing the compliance manager queue 612 according to the disclosed embodiments. A compliance manager logs into its portal and sees the compliance manager queue 612 as shown. Compliance manager queue 612 shows all the healthcare workers 204 that require compliance verification. This view also shows if anything is amiss in the documents requested from the suppliers 202. The compliance manager selects the candidate from the queue to view and approve all documents submitted for the onboard to move further along process 600.

FIG. 21 illustrates a screen 2100 for individual health document review and approval according to the disclosed embodiments. FIG. 22 illustrates a screen 2200 for individual HR document review and approval according to the disclosed embodiments. Screens 2100 and 2200 are broken into two parts. The top parts 2102 and 2202 are dynamically constructed from the healthcare facility configuration using the profile elements for the documented proof that is mandated. The bottom parts 2104 and 2204 are dynamically constructed from the healthcare facility configuration using the checklist created to ensure that the mandated steps are all verified before allowing a profile to be presented to the healthcare facility's internal HR and employee health administrators for another level of approval.

Similar to the compliance manager login portal, MSP platform 100 also includes portals for a facility's HR and health services team for validating adherence to the facility's internal rules. The approval process used by the HR and health service personnel is identical to the compliance manager functions. Thus, these steps are skipped here for brevity.

Figure 23:
FIG. 23 illustrates a screen of the MSP view of an orientation queue according to the disclosed embodiments.

After all documents are reviewed and approved, the next segment of process 600 is to schedule the healthcare worker 204 to attend orientation. FIG. 23 shows the screen 2300 of the progression as viewed by the administrator of the MSP 106.

Figure 24:
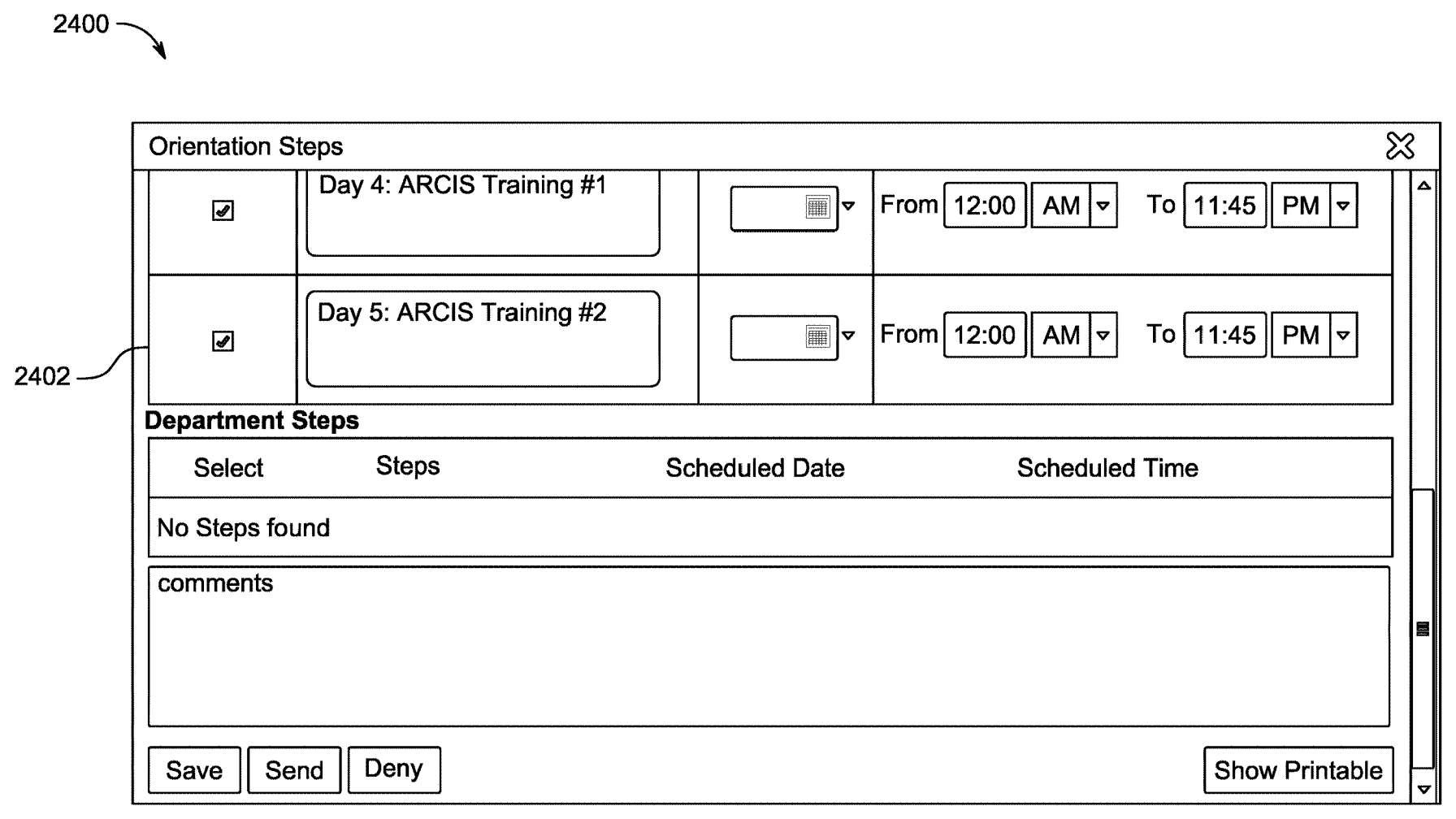
Figure 25:
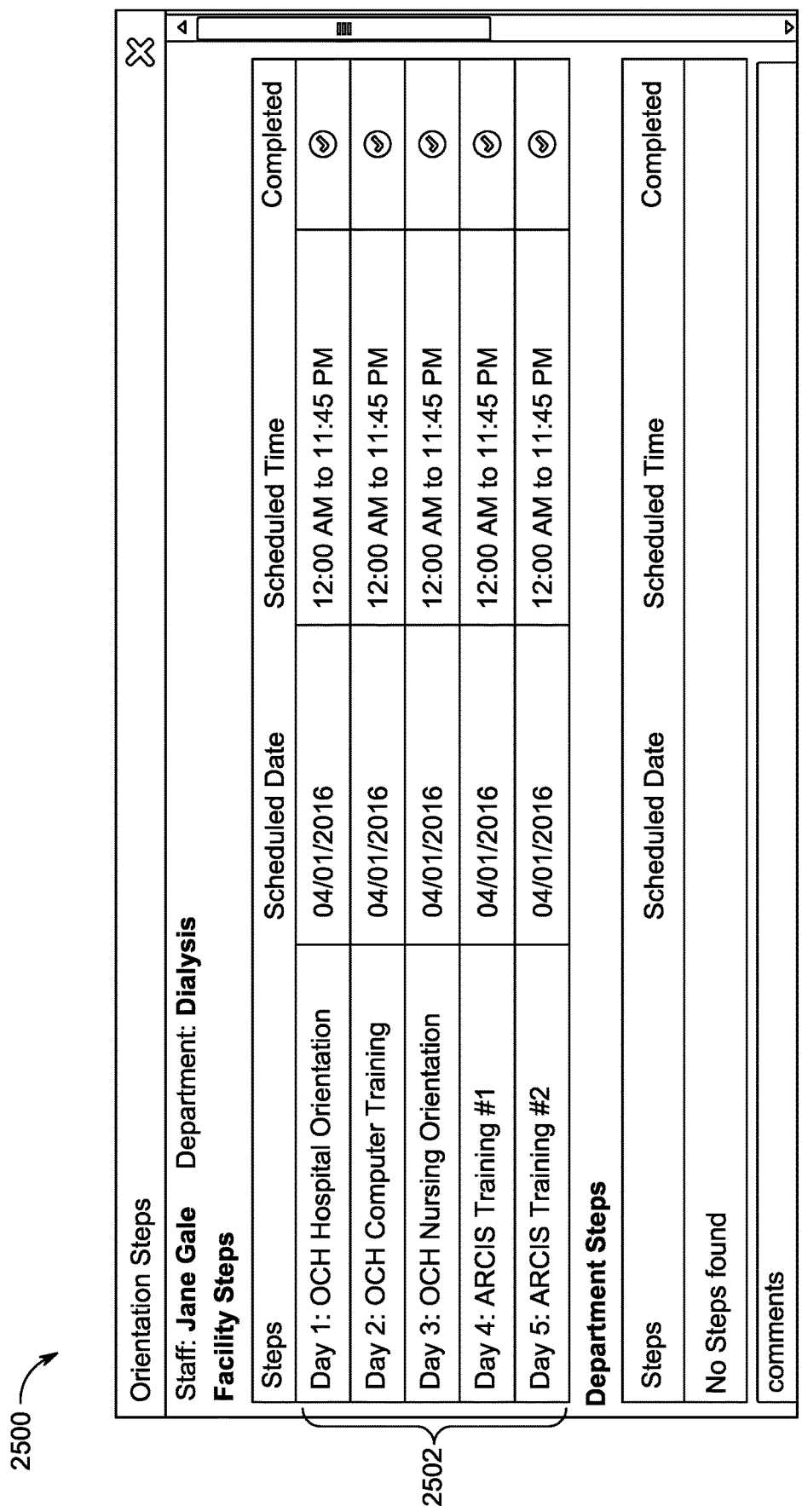
FIG. 25 illustrates the screen showing verification of orientation steps according to the disclosed embodiments.
Figure 27:
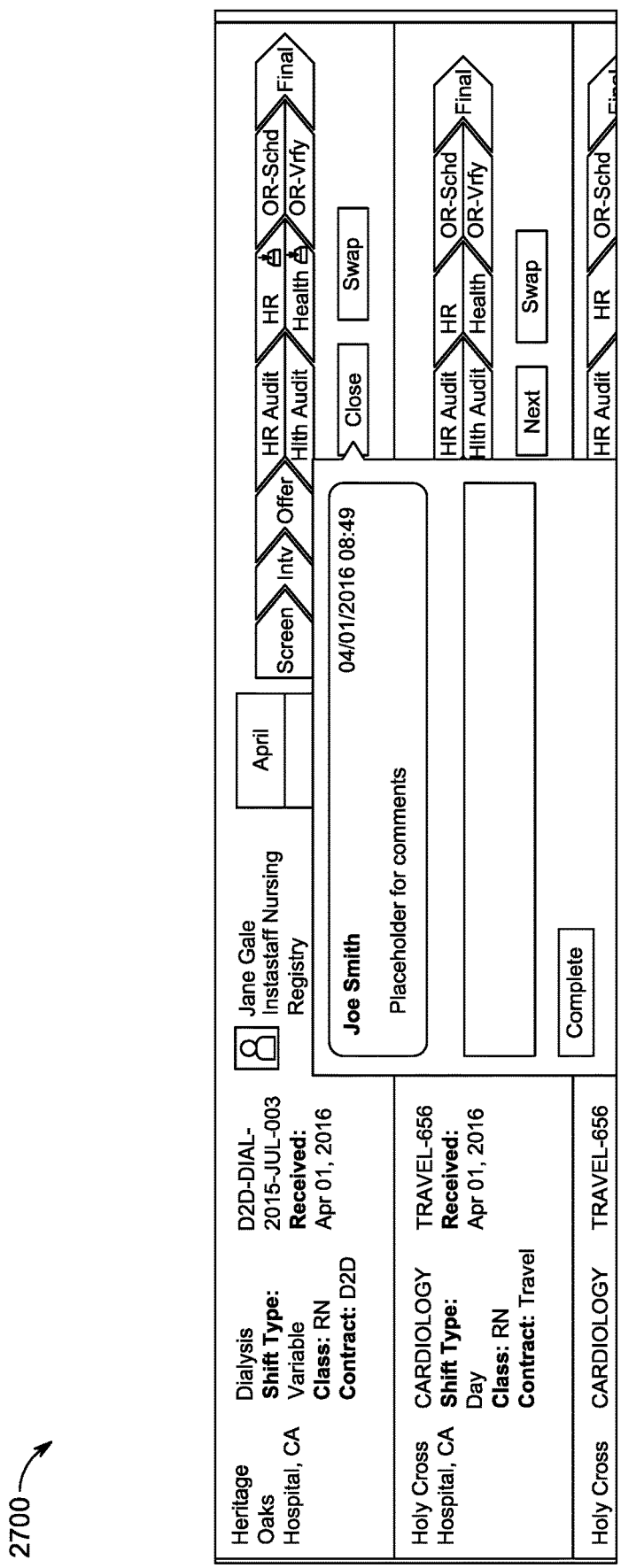
FIG. 27 illustrates a screen showing final step to mark onboard completed according to the disclosed embodiments.

FIG. 24 illustrates a screen 2400 showing the MSP admin creating an orientation schedule 2402 according to the disclosed embodiments. FIG. 25 illustrates the screen 2500 showing verification of orientation steps 2502 according to the disclosed embodiments. FIG. 26 illustrates the screen 2600 for the MSP view of completion of orientation according to the disclosed embodiments. FIG. 27 illustrates a screen 2700 showing final step to mark onboard completed according to the disclosed embodiments.

Once in orientation queue 618, the MSP Staffing Manager, or another stakeholder, will create an orientation schedule 2402 as shown. The schedule is automatically created from the template earlier created for the healthcare facility 102 as part of the facility configuration. The schedule and all its elements are editable. When the dates are updated, the schedule is sent over to supplier 202 and healthcare worker 204. Referring to FIG. 25, each orientation step 2502 is verified as complete once it is completed.

Upon successful completion of orientation, the healthcare worker profile is staged for the final approval segment. When the onboard is marked completed, the healthcare worker 204 is added to the qualified staff pool as shown in FIG. 27. The staff can be monitored for assignments and continued compliance. At this time, the healthcare worker 204 can be assigned shifts.

Thus, the disclosed embodiments provide an automated process to begin, plan, and track the identification and certification of a healthcare worker. Each segment of process 600 is tracked so that the position of the healthcare worker profile within the MSP platform 100 is known. Further, information is provided in a uniform format across all entities.

Figure 28:
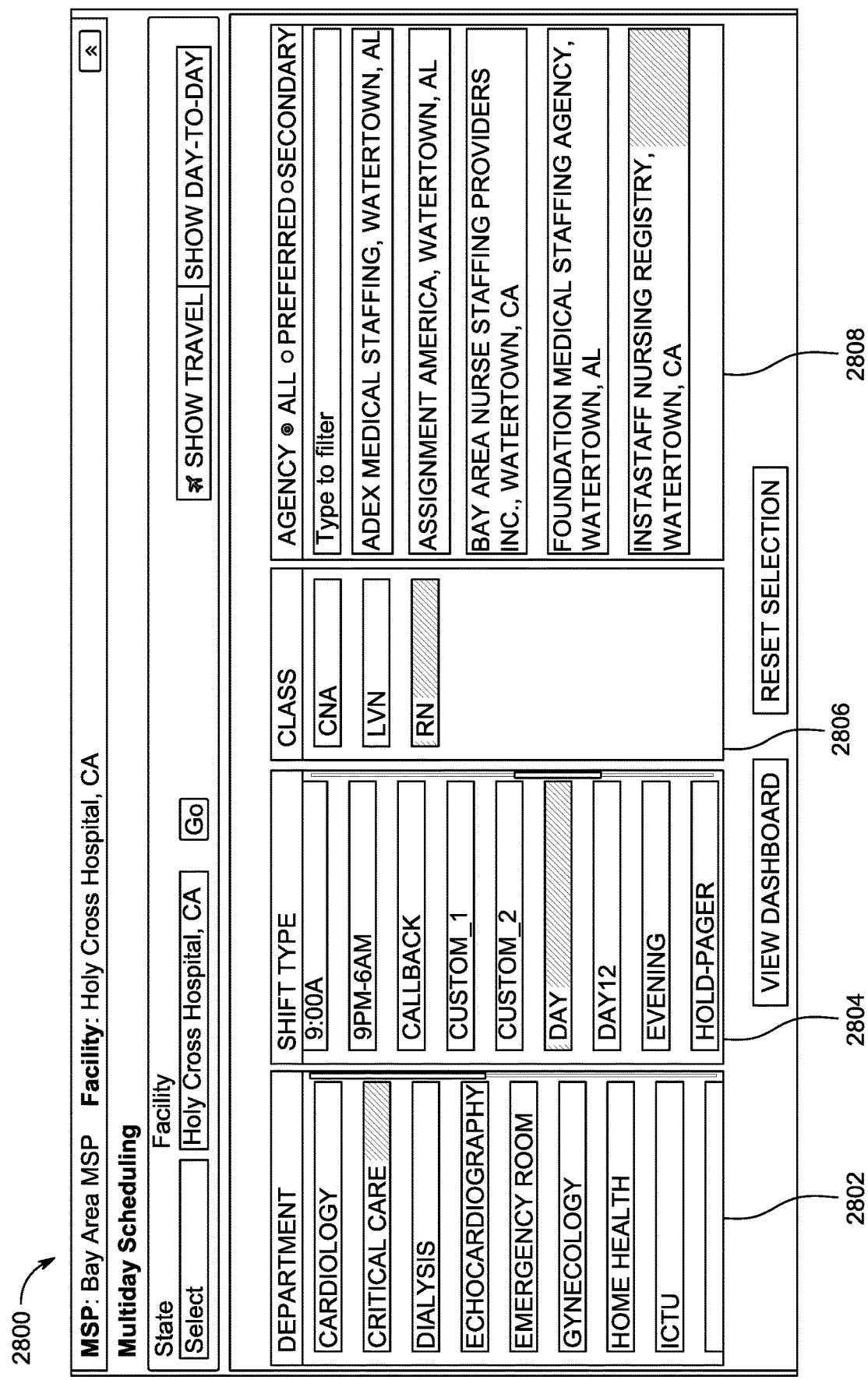
FIG. 28 illustrates a selection criteria screen for creation of a 5-dimensional view according to the disclosed embodiments.

MSP platform 100 also may be used as a collaborative scheduling platform that allows multiday scheduling. This method of scheduling day-to-day shifts provides a 5-dimensional matrix making it very easy to schedule shifts for an entire facility on simply one single screen. As shown in FIG. 28, one starts by selecting all departments, shift types, job class, and a set of suppliers from the supplier ecosystem. Suppliers can be selected incrementally i.e. more suppliers can be added later to the multiday day-to-day job order. The resulting 5-dimensional view organizes the result set by departments, job classes, available healthcare workers, shift-types, and dates. Therefore, hundreds of shifts can be filled on a single screen in minutes. In the background, a separate job-order for multiday day-to-day shifts is created for each healthcare worker. Optionally, instead of choosing any specific healthcare worker, a generic broadcast can be sent for desired number of healthcare workers required for a given day for the combination of department, job class, shift-type, and dates.

This same mechanism can be used for travel staff (as against day-to-day staff) as well. The only difference is that the travel staff is instantly confirmed as they are pre-booked for a specific contract period, whereas the day-to-day staff is requested for reciprocating with a confirmation by either the healthcare worker or its supplier representative.

FIG. 28 illustrates a selection criteria screen 2800 for creation of a 5-dimensional view according to the disclosed embodiments. Criteria are shown for selection in fields. One selects data from the fields to build the view. Screen 2800 includes department field 2802, shift type field 2804, class field 2806, and agency field 2808. Other information may be shown on screen 2800 pertaining the healthcare facility 102 and the like.

Figure 29:
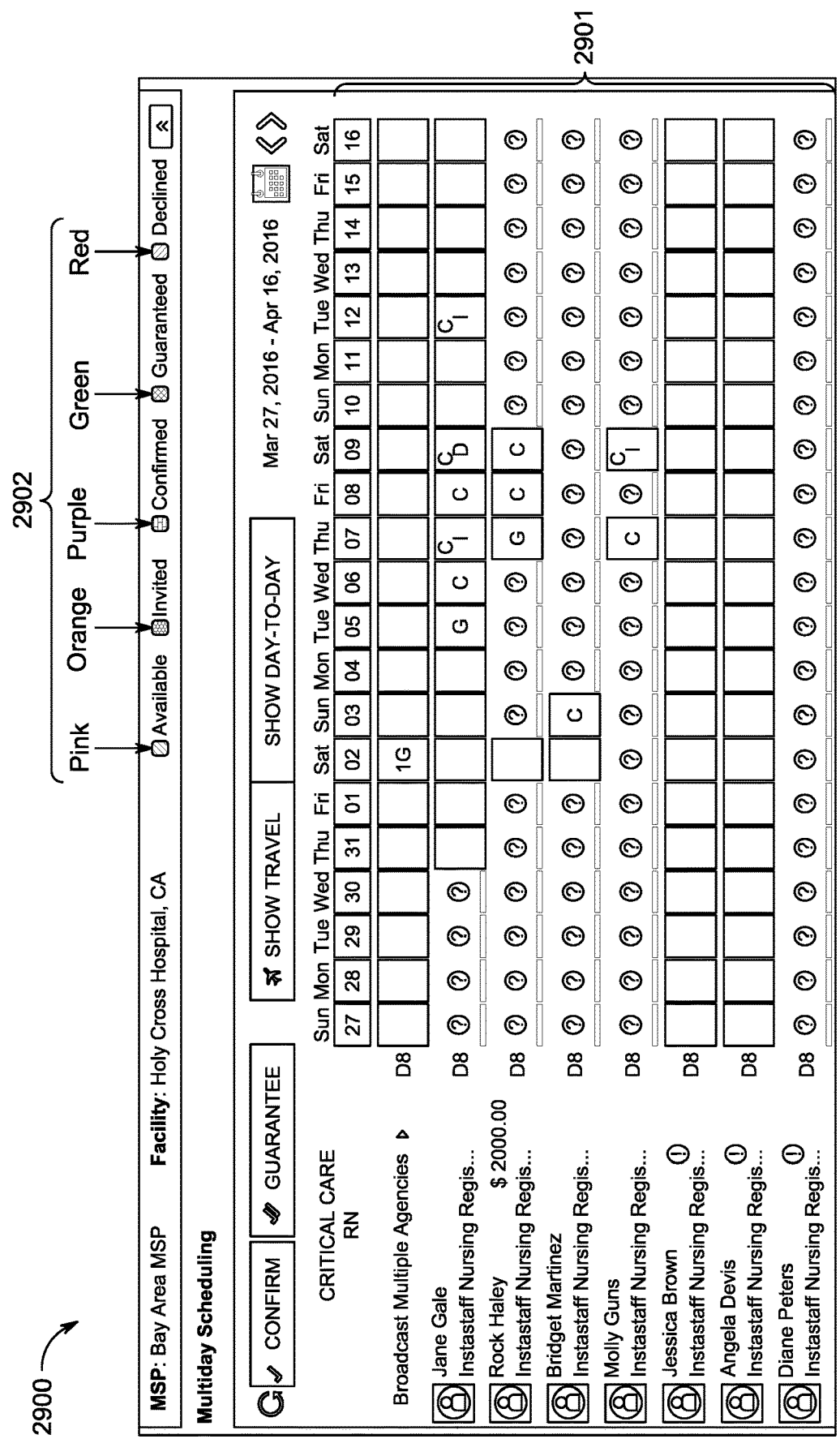
FIG. 29 illustrates a screen of the 5-dimensional view on executing searches according to the disclosed embodiments.

FIG. 29 illustrates a screen 2900 of the 5-dimensional view on executing searches according to the disclosed embodiments. Each cell 2901 in the screen 2900 is clickable to do additional actions such as cancel a shift or cancel a specific healthcare worker (but keep the shift). Color codes 2902 explain the status of each cell. For example, orange implies that a specific healthcare worker has been invited and waiting acceptance by the worker or its supplier. Green indicates that the position was successfully filled. Red indicates that the shift was declined for the named healthcare worker. Pink indicates that the healthcare worker calendar shows that the slot coinciding with the shift-type is marked as available for taking new shifts. Another availability status is denoted by a question mark in the cell, which means that the slot is neither blocked nor available. In other words, the disposition of the slot is ambiguous and may possibly require a call to the healthcare worker to confirm availability.

Figure 30:
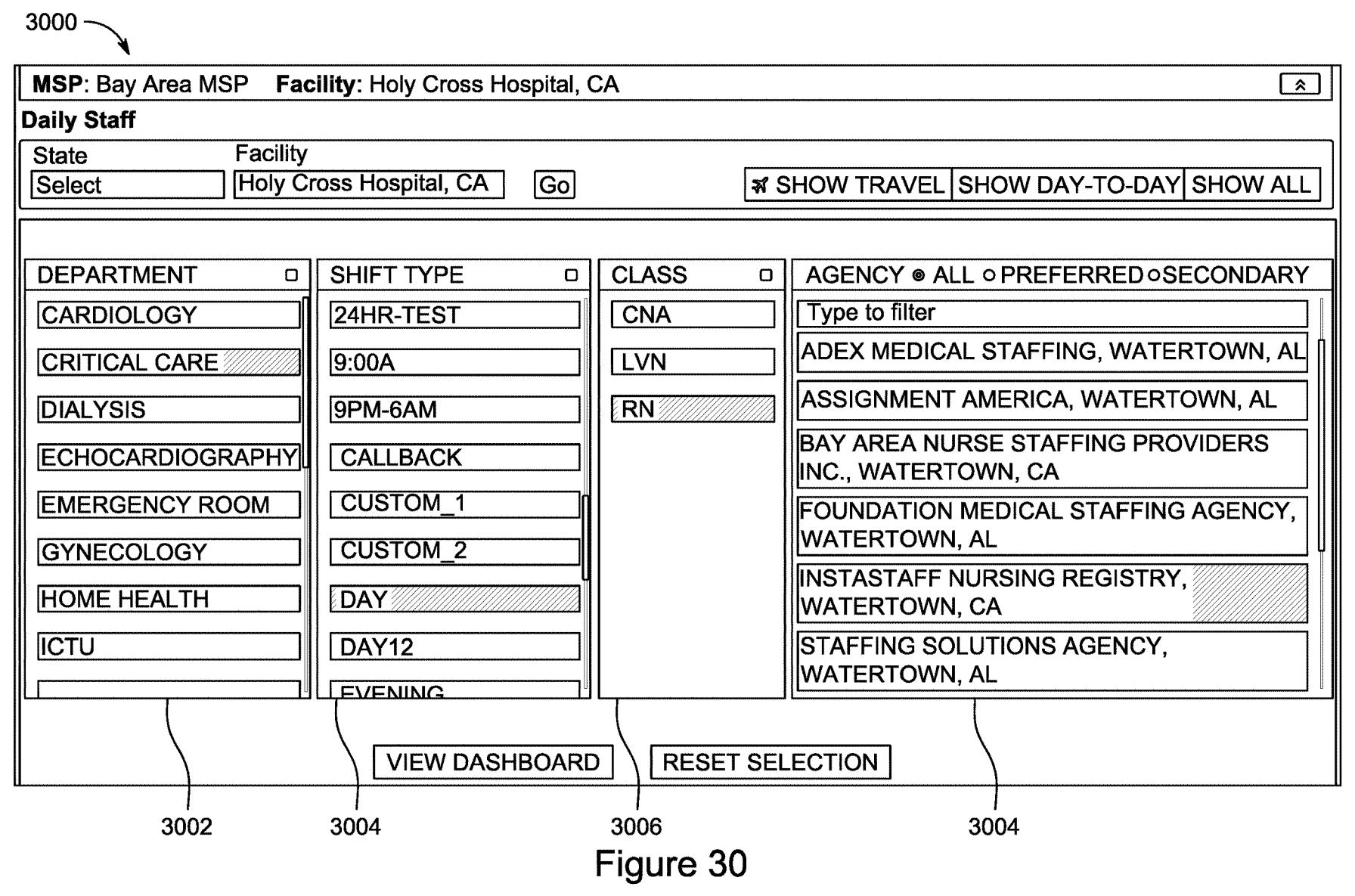

The MSP platform 100 also enables single day scheduling, or the daily view. This method of scheduling day-to-day shifts provides a 3-dimensional matrix making it very easy to schedule shifts for an entire facility by dynamically creating a single screen. As shown in FIG. 30, one starts by selecting all departments, shift types, job class, and a set of suppliers from the supplier ecosystem. Suppliers 202 can be selected incrementally, i.e. more suppliers can be added later to the day-to-day job order.

FIG. 30 illustrates a screen 3000 of selection criteria for creation of a 3-dimensional view according to the disclosed embodiments. Criteria are shown for selection in fields. One selects data from the fields to build the view. Screen 3000 includes department field 3002, shift type field 3004, class field 3006, and agency field 3008. Other information may be shown on screen 3000 that pertains to the healthcare facility 102 and the like.

Figure 31:
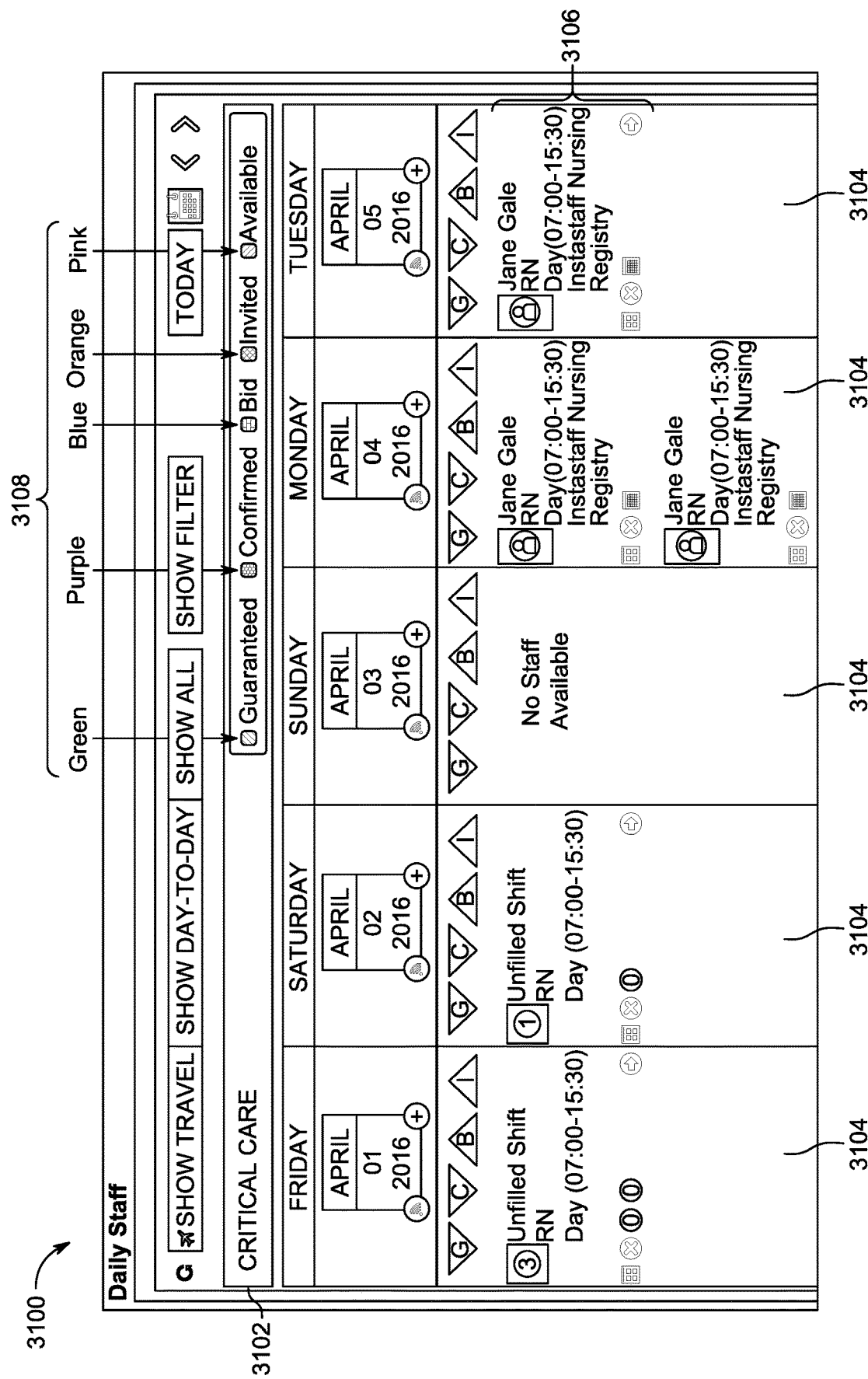
FIG. 31 illustrates a screen for the 3-dimensional view on executing searches according to the disclosed embodiments.

FIG. 31 illustrates a screen 3100 for the 3-dimensional view on executing searches according to the disclosed embodiments. The resulting 3-dimensional view shown is organized by departments 3102, dates (as swim lanes) 3104, and available healthcare workers (identifying both the shift-types and job-class) 3106. This feature provides the ability to view daily outstanding needs and contingent healthcare workers working on that day created by any of 3 methods discussed in this document. Requesting specific healthcare workers for a specific day will create a new day-to-day job order for only that day and shift-type. Optionally, instead of choosing any specific healthcare worker, a generic broadcast can be sent for desired number of healthcare workers required for a given day for the combination of department, job class, and shift-type. Colors 3108 also are used to indicate status of the shifts and the workers shown therein.

This same mechanism can be used for travel staff (as against day-to-day staff) as well. The only difference is that the travel staff is instantly confirmed as they are pre-booked for a specific contract period, whereas the day-to-day staff is requested for reciprocal confirmation by either the healthcare worker or its supplier representative.

Figure 32:
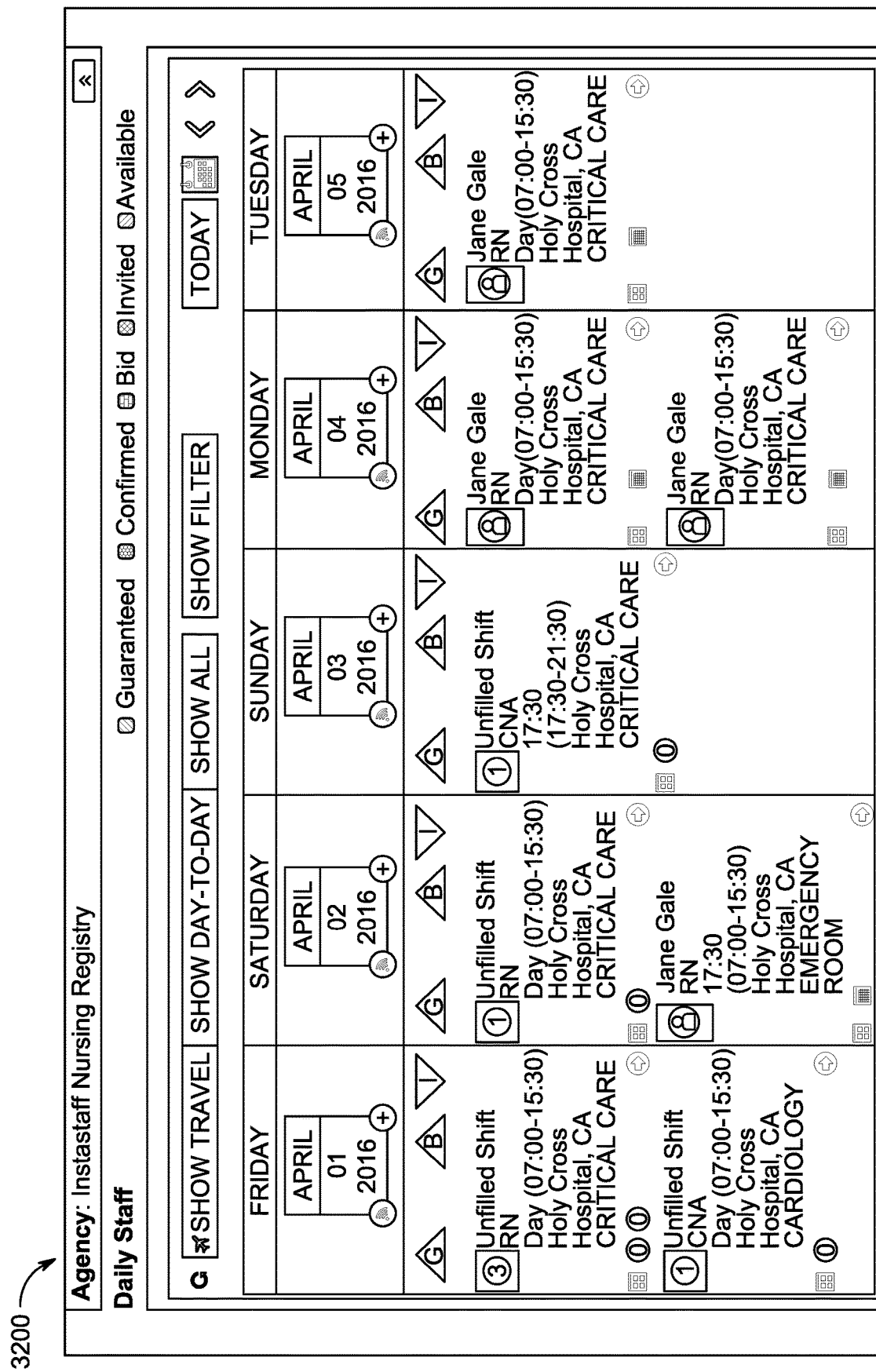
FIG. 32 illustrates a screen for a consolidated view for a supplier from all healthcare facilities according to the disclosed embodiments.

FIG. 32 illustrates a screen 3200 for a consolidated view for a supplier 202 from all healthcare facilities 102 according to the disclosed embodiments. Supplier view is basically a catchall bucket. Day-to-day shift requests for all health facilities, for all shift types and job-classes, are presented in the day column. This simplified view allows a supplier to see the demand-by-date in one consolidated queue from all healthcare facilities. Therefore, the supplier 202 can also see conflicting requests for same person, or more demand for a given day, and can adjust the resources accordingly, while also offering replacement candidates in cases where named-workers in job orders cannot be made available because of multiple opportunities.

The MSP platform 100 also enables VoIP-enabled multi-day scheduling. In this method of scheduling, a multidimensional search on healthcare workers is performed based on department, job class, shift-type, and one or more dates as shown. This feature is different from the multiday scheduling discussed earlier where a calendar based availability screen is created for the entire staff pool qualified for the shift. In the current VoIP-based scenario, the available staff is shown based on dates and other parameters provided, which keeps the view limited in scope, and contextualized to specific parameters.

Figure 33:
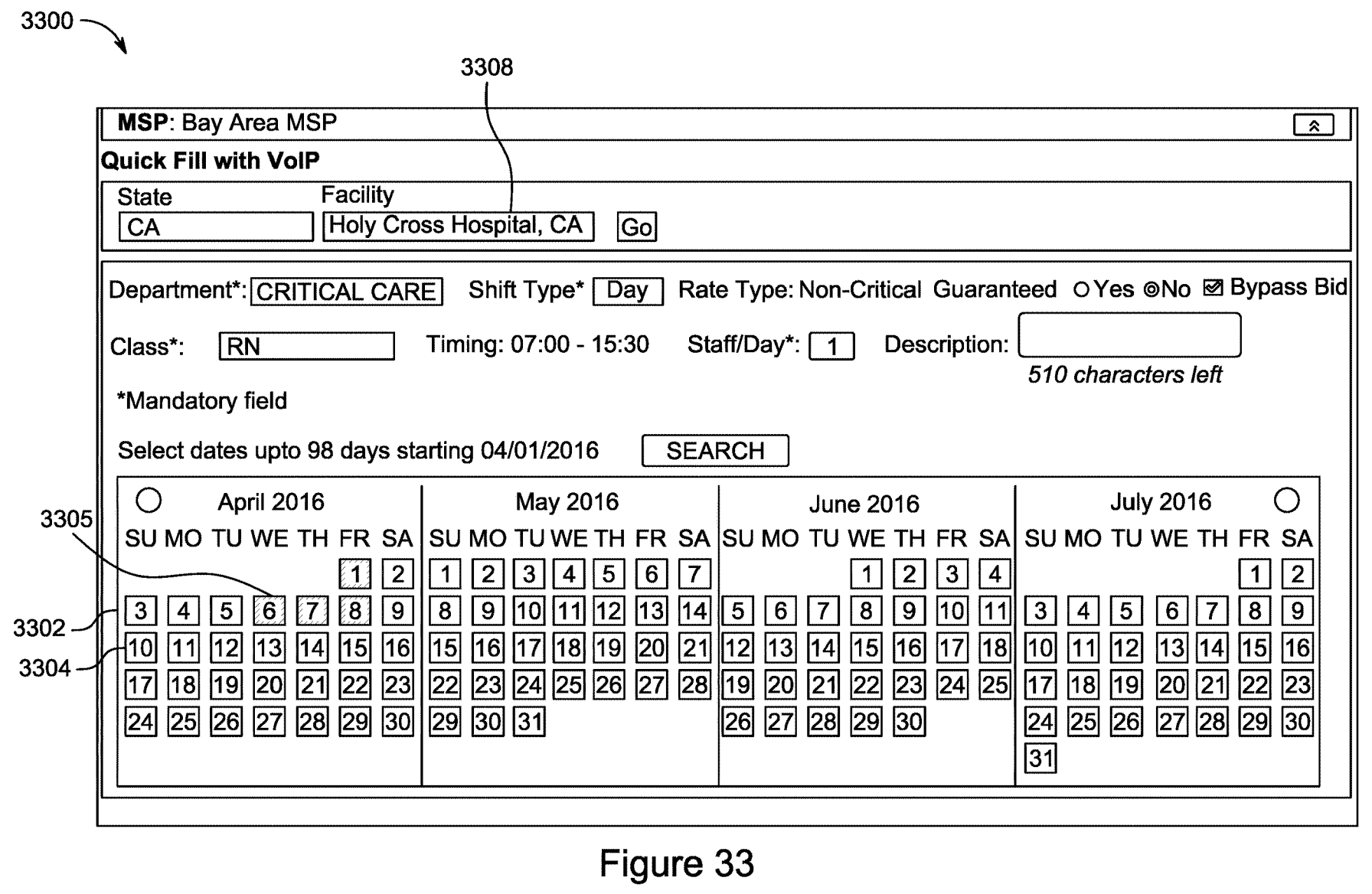

FIG. 33 illustrates a search screen 3300 for VoIP multiday scheduling according to the disclosed embodiments. There are differences from the previous screens for multiday and daily scheduling disclosed above. Screen 3300 includes months field 3302 showing the months available for scheduling. Within the months, dates 3304 also are shown for selection. Selected dates 3305 also may be shown as blacked out or colored in some manner. The search may be done for a specific healthcare facility 102, as specified in facility field 3308.

Figure 34:
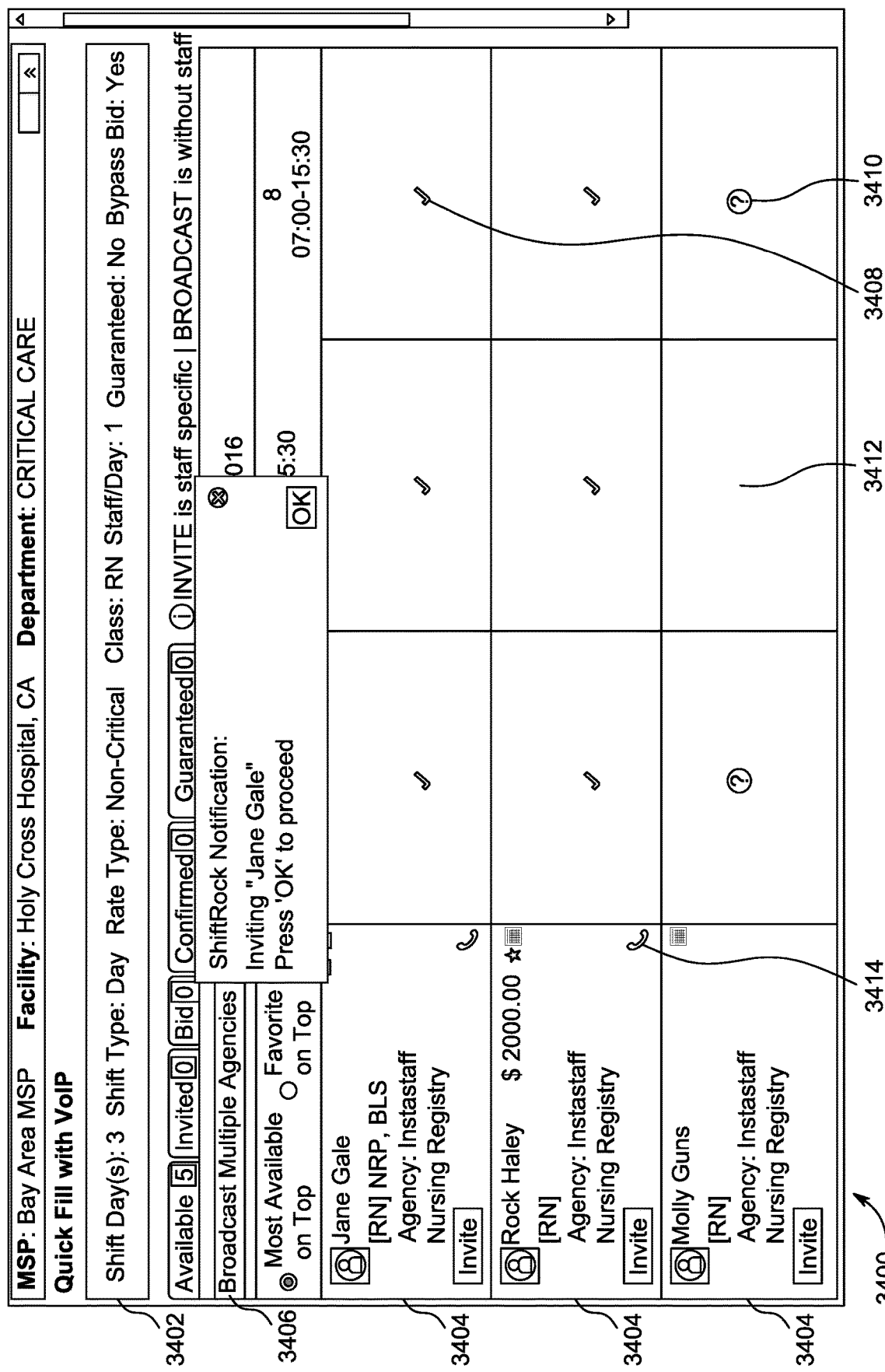
FIG. 34 illustrates a MSP pre-VoIP view screen for VoIP-enabled invitations for day-to-day job orders according to the disclosed embodiments.

FIG. 34 illustrates a MSP pre-VoIP view screen 3400 for VoIP-enabled invitations for day-to-day job orders according to the disclosed embodiments. The healthcare workers 204 satisfying the search criteria specified in screen 3300 are listed in view screen 3400 along with their availability marked for each day included in the day-to-day multiday job order. The job order may be reflected by field 3402, which lists the parameters for the job order. Candidates 3404 are shown along with a button 3406 to broadcast the job order across multiple agencies.

When the entire shift period matches the healthcare worker availability in the worker's virtual calendar, the related slot is represented by a green checkmark 3408. A worker has a single virtual calendar shared across all employers, and this prevents scheduling conflicts. If the entire shift period is undeclared or unspecified for availability, then such slots are depicted by a question mark 3410 implying that the candidate may be available and needs to be contacted for confirmation before allocating the candidate to the shift. If a worker is already unavailable because of leave or blocked by another fully or partially overlapping shift then the corresponding cell is shown as blank 3412 meaning unavailable. When multiple candidates are available to fill a multiday shift, then the days can be distributed among several healthcare workers. This is done on the facility side by removing specific days by clicking on the check mark or the question mark in each cell, which excludes the day from being allocated to the healthcare worker. In this fashion, opportunities can be fairly distributed.

A phone icon 3414 is provided against an available healthcare worker if all corresponding slots are checked. If there are any question marks, then those days need to be first removed. The MSP platform 100 can directly contact either the candidate or its representative supplier via VoIP. The VoIP logic automatically announces all the parameters of the shift along with the name of the candidate selected, and the recipient of the call can respond by either declining or accepting the shift by appropriately punching the right options announced on their phone keypad. When multiple suppliers 202 are processing the same order over VoIP, and if the job-order is designated as BID then multiple candidates can be queued in the facility's day-to-day queue; from these submissions only the order-provided number of workers can be CONFIRMED or GUARANTEED while sending an automated declination to others. If the order type is either CONFIRMED or GUARANTEED, then acceptance of any day within a multiday day-to-day job order is awarded on first come first serve basis and all new acceptances blocked as soon as the shift limit for a specific day is met.

Figure 35:
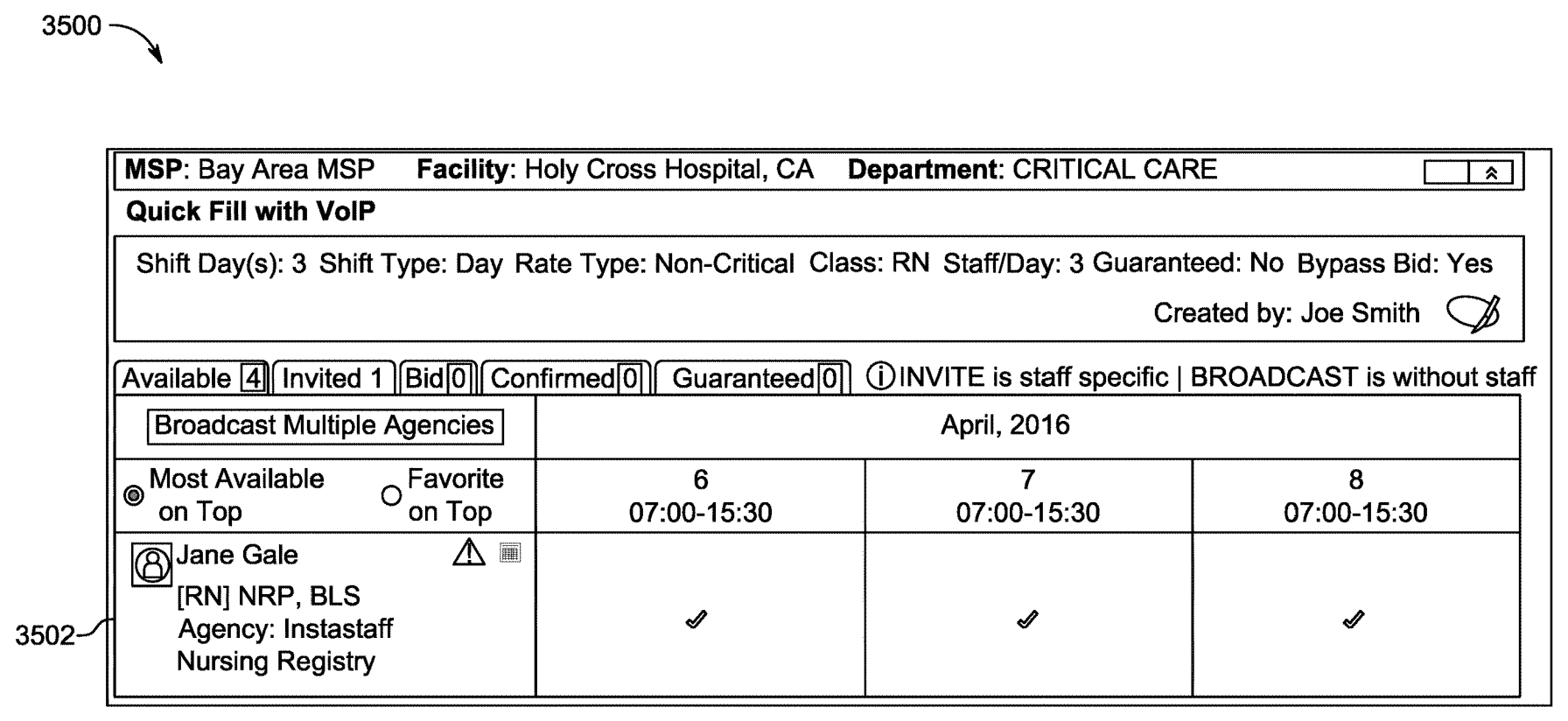
Figure 36:
FIG. 36 illustrates the supplier view screen when the healthcare worker is moved to the BID queue on accepting the shift(s) according to the disclosed embodiments.
Figure 37:
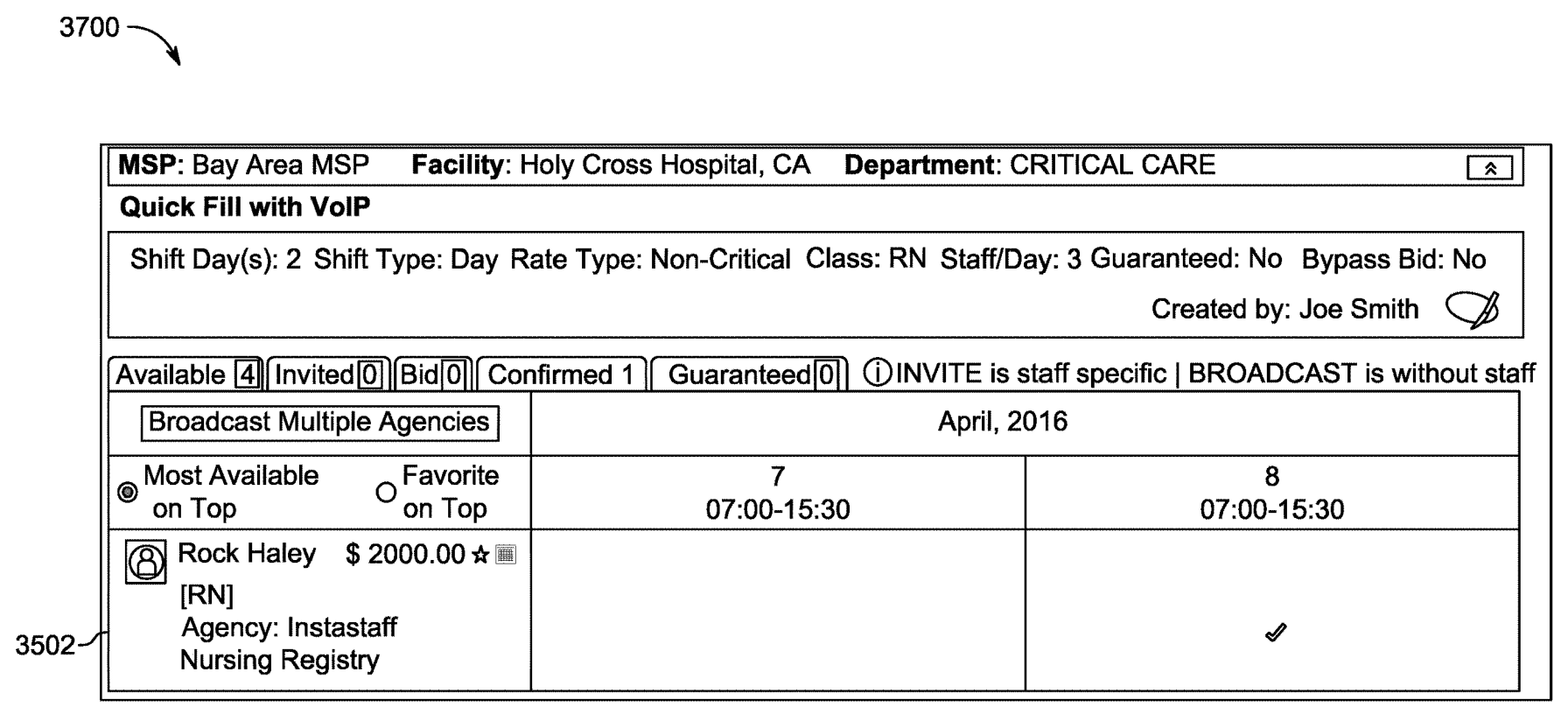

FIG. 35 illustrates the MSP view screen 3500 showing the healthcare worker 3502 in the invited queue according to the disclosed embodiments. FIG. 36 illustrates the supplier view screen 3600 when the healthcare worker 3502 is moved to the BID queue on accepting the shift(s) according to the disclosed embodiments. FIG. 37 illustrates the supplier view screen 3700 when the healthcare worker 3502 is moved to the confirmed queue on accepting the shift(s) according to the disclosed embodiments. These screens are disclosed in greater detail below.

These figures highlight the provision for sending manual invites. Manual invites are helpful to suppliers 202 by providing facility-like features in declining certain days for certain employees. This feature helps in distributing shifts across multiple healthcare workers 204 while also providing the ability to decline candidates that were available at the time of multiday day-to-day job-order creation, but are no longer available at the time of accepting the shift.

When multiple suppliers are processing the same order, and if the job-order is designated as BID, then multiple candidates can be queued in the facility's day-to-day queue. From these submissions, only the order-provided number of workers can be selected while sending an automated declination to others. FIG. 36 shows the supplier view when accepting a BID shift in a multiday day-to-day job order.

If the order type is either CONFIRMED or GUARANTEED, then acceptance of any day within a multiday day-to-day job order is awarded on first come first serve basis and all new acceptances are blocked as soon as the shift limit for a specific day is met. FIG. 37 shows the supplier view when accepting a CONFIRMED shift in a multiday day-to-day job order. When shifts are accepted using either VoIP or manually, a backing timecard is immediately created for CONFIRMED or GUARANTEED shift type. This timecard is shown when the healthcare worker 3502 arrives onsite at the facility. The timecard is available to the healthcare workers on their mobile device.

It is not always necessary to send manual invites or use VoIP. A multiday day-to-day job order without candidates can be send using the BROADCAST mechanism. In this case, the suppliers can fill the candidates of their choice from all available healthcare workers. Regardless of whether broadcast was used or workers invited by name, the AVAILABLE slot shown in the figures above always scans the system to check for new availability. Therefore, these types of orders are considered to be real-time orders as the order is constantly aware about the changing availability across the ecosystem regardless of which supplier is seeing the job order. Each candidate in the AVAILABLE pool is tagged with a PROPOSE button. A PROPOSE is identified on the MSP side with a different color, such as a yellow background, to indicate the proposed candidate 3502 was in response to a broadcasted job-order, or was offered in place of another worker originally named in the job order. However, the AVAILABLE tab only shows the workers who have completed onboard with a specific hospital associated with the order and the onboard was done in the context of the supplier. This creates a dedicated relationship between the supplier and the healthcare facility in the context of the named candidate such that no other supplier can propose the same candidate.

Thus, the disclosed embodiments allow for scheduling across multiple facilities, suppliers and pools of healthcare workers. Information on shifts and filled slots is updated instantaneously. A healthcare facility may use the disclosed view screen to select and notify candidates of available shifts. Several suppliers may access the same screens such that the scheduling information is consistent throughout the system. Conflicts are avoided using the disclosed platform.

Figure 38:
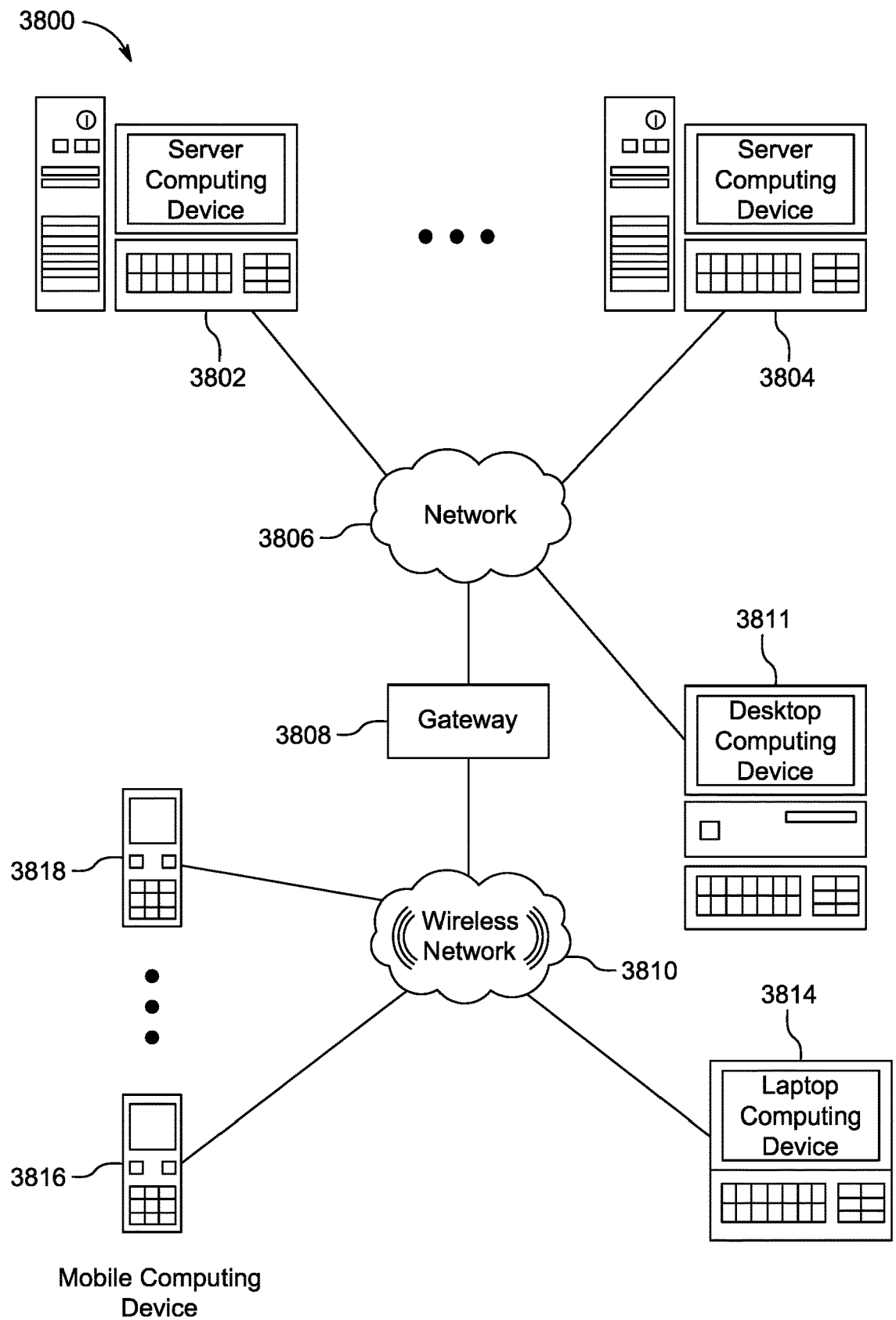
FIG. 38 illustrates an MSP system.

FIG. 38 depicts a managed service provider system 3800 for managing collaborative credentialing, compliance, and scheduling of contingent healthcare workers by multiple MSPs and healthcare facilities according to the disclosed embodiments. Other components may be included in system 3800 not shown in FIG. 38. The disclosure of FIG. 38 is shown for clarity and may include any of these additional components to perform the functionality disclosed herein.

System 3800 may include local area networks (LAN) and wide area network (WAN) shown as network 3806 and wireless network 3810. Gateway 3808 is configured to connect remote or different types of networks together, as well as client computing devices 3812-3818 and server computing devices 3802-3804.

Client computing devices 3812-3818 may include any device capable of receiving and sending data over a network, such as wireless network 3810. Devices 3812-3818 may include portable devices such as cellular telephones, smart phones, radio frequency-enabled devices, personal digital assistants, handheld computers, tablets, laptop computers, wearable computers and the like. Devices 3812-3818 also may include any computing device that connects to a network using a wired communications medium such as personal computers, multiprocessor systems, microprocessor-based or programmable consumer electronics, network personal computers and the like.

Client computing devices 3812-3818 also may be web-enabled client devices that include a browser application configured to receive and to send web pages, web-based messages and the like. The browser application may be configured to receive and display graphic, text, multimedia, or the like, employing virtually any web based language, including a wireless application protocol messages (WAP), or the like. In one embodiment, the browser application may be enabled to employ one or more of Handheld Device Markup Language (HDML), Wireless Markup Language (WML), WMLScript, JavaScript, Standard Generalized Markup Language (SMGL), HyperText Markup Language (HTML), eXtensible Markup Language (XML), or the like, to display and send information.

Client computing devices 3812-3818 also may include at least one other client application that is configured to receive content from another computing device, including, without limit, server computing devices 3802-3804. The client application may include a capability to provide and receive textual content, multimedia information, or the like. The client application may further provide information that identifies itself, including a type, capability, name, or the like. In one embodiment, client devices 3812-3818 may uniquely identify themselves through any of a variety of mechanisms, including a phone number, mobile identification number (MIN), an electronic serial number (ESN), mobile device identifier, network address, such as IP (Internet Protocol)

address, media access control (MAC) layer identifier, or other identifier. The identifier may be provided in a message, or the like, sent to another computing device.

Client computing devices 3812-3818 may also be configured to communicate a message, such as through email, short message service (SMS), multimedia message service (MMS), instant messaging (IM), internet relay chat (IRC), Mardam-Bey's IRC (mIRC), Jabber, or the like, to another computing device.

Client devices 3812-3818 may further be configured to include a client application that enables the user to log into a user account that may be managed by another computing device. Such a user account, for example, may be configured to enable the user to receive emails, send/receive IM messages, SMS messages, access selected web pages, download scripts, applications, or a variety of other content, or perform a variety of other actions over a network. Management of messages or otherwise accessing and/or downloading content, may also be performed without logging into the user account. Thus, a user of client devices 3812-3818 may employ any of a variety of client applications to access content, read web pages, receive/send messages, or the like.

In one embodiment, for example, the user may employ a browser or other client application to access a web page hosted by a Web server implemented as server computing device 3802. Messages received by client computing devices 3812-3818 may be saved in non-volatile memory, such as flash and/or PCM, across communication sessions and/or between power cycles of client computing devices 3812-3818.

Wireless network 3810 may be configured to couple client devices 3814-3818 to network 3806. Wireless network 3810 may include any of a variety of wireless sub-networks that may further overlay stand-alone ad-hoc networks, and the like, to provide an infrastructure-oriented connection for client devices 3814-3818. Such sub-networks may include mesh networks, Wireless LAN (WLAN) networks, cellular networks, and the like. Wireless network 3810 may further include an autonomous system of terminals, gateways, routers, and the like connected by wireless radio links, and the like. These connectors may be configured to move freely and randomly and organize themselves arbitrarily, such that the topology of wireless network 3810 may change rapidly.

Wireless network 3810 may further employ a plurality of access technologies including 2nd (2G), 3rd (3G), 4th (4G), 5th (5G) and the like generation radio access for cellular systems, WLAN, Wireless Router (WR) mesh, and the like. Access technologies such as 2G, 3G, 4G, 5G and future access networks may enable wide area coverage for mobile devices, such as client devices 3814-3818 with various degrees of mobility. For example, wireless network 3810 may enable a radio connection through a radio network access such as global system for mobile communication (GSM), general packet radio services (GPRS), enhanced data GSM environment (EDGE), WEDGE, Bluetooth, high speed downlink packet access (HSDPA), universal mobile telecommunications system (UMTS), Wi-Fi, Zigbee, wideband code division multiple access (WCDMA), and the like. In essence, wireless network 3810 may include virtually any wireless communication mechanism by which information may travel between client devices 3802-3804 and another computing device, network, and the like.

Network 3806 is configured to couple one or more servers depicted in FIG. 38 as server computing devices 3802-3804 and their respective components with other computing devices, such as client device 3812, and through wireless network 3810 to client devices 3814-3818. Network 3806 is enabled to employ any form of computer readable media for communicating information from one electronic device to another. Network 3806 also may include the Internet in addition to local area networks (LANs), wide area networks (WANs), direct connections, such as through a universal serial bus (USB) port, other forms of computer-readable media, or any combination thereof. On an interconnected set of LANs, including those based on differing architectures and protocols, a router acts as a link between LANs, enabling messages to be sent from one to another. Network 3806 may include any communication method by which information may travel between computing devices. Additionally, communication media typically may enable transmission of computer-readable instructions, data structures, program modules, or other types of content, virtually without limit. By way of example, communication media includes wired media such as twisted pair, coaxial cable, fiber optics, wave guides, and other wired media and wireless media such as acoustic, RF, infrared, and other wireless media.

Figure 39:
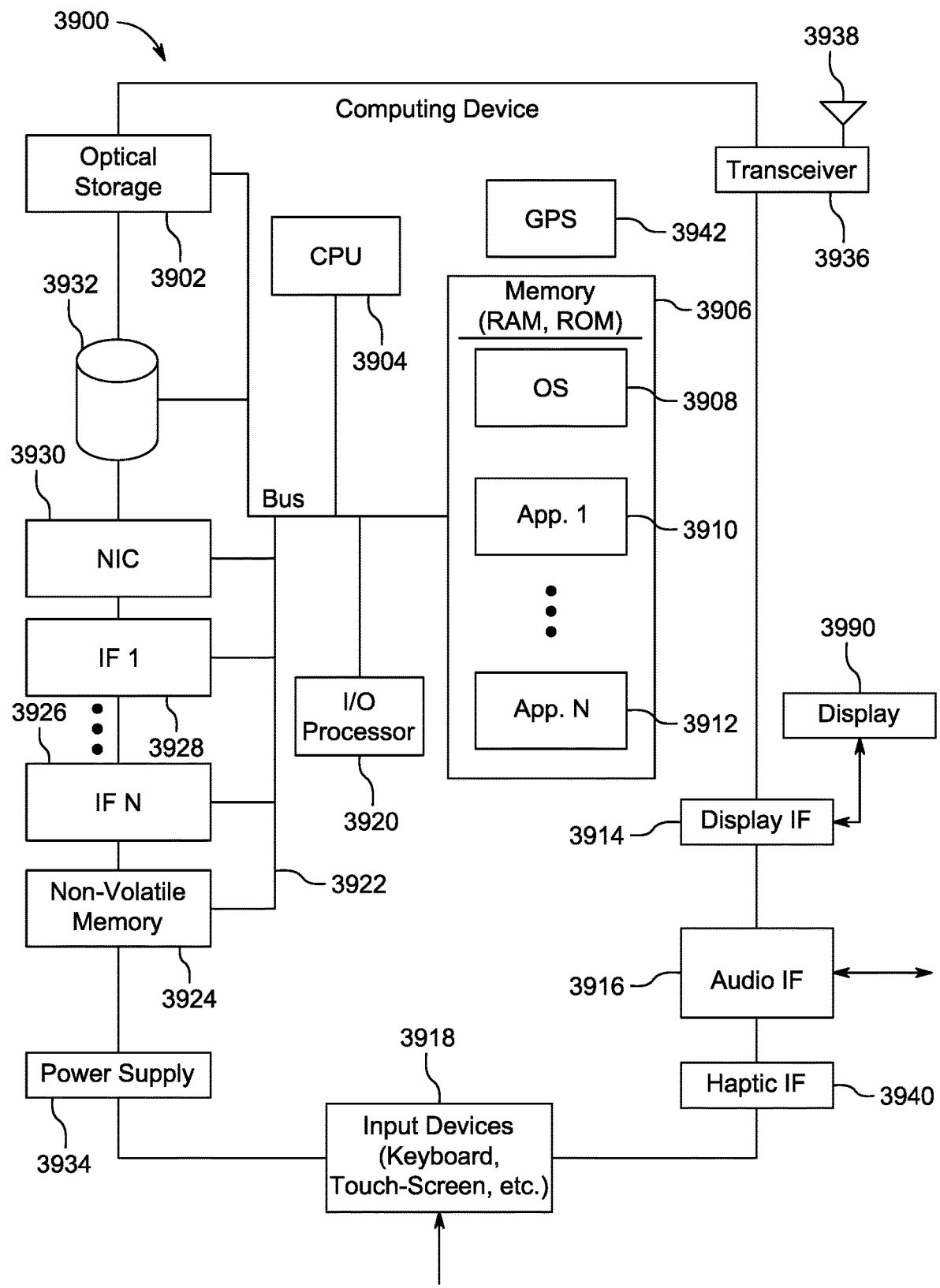
FIG. 39 illustrates a computing device configured to execute the functionality disclosed in the MSP system.

FIG. 39 depicts a computing device 3900 configured to execute the functionality disclosed in greater detail below. Computing device 3900 may communicate with other devices over system 3800 to perform the functions needed for managing collaborative credentialing, compliance, and scheduling of contingent healthcare workers by multiple MSPs and healthcare facilities. Computing device 3900 may be representative of any of the computing devices shown in FIG. 38.

Computing device 3900 includes optical storage 3902, central processing unit (CPU) 3904, memory module 3906, display interface 3914, audio interface 3916, input devices 3918, input/output (I/O) processor 3920, bus 3922, non-volatile memory 3924, various other interfaces 3926-3928, network interface card (NIC) 3930, hard disk 3932, power supply 3934, transceiver 3936, antenna 3938, haptic interface 3940, and global positioning system (GPS) unit 3942. Memory module 3906 may include software such as operating system (OS) 3908, and a variety of software application programs and/or software modules/components 3910-3912. Such software modules and components may be stand-alone application software or be components, such as DLL (Dynamic Link Library) of larger application software.

Computing device 3900 may also include other components not shown in FIG. 39. For example, computing device 3900 may further include an illuminator (for example, a light), graphic interface, and portable storage media such as USB drives. Computing device 3900 may also include other processing units, such as a math co-processor, graphics processor/accelerator, and a Digital Signal Processor (DSP).

Optical storage device 3902 may include optical drives for using optical media, such as CD (Compact Disc), DVD (Digital Video Disc), and the like. Optical storage devices 3902 may provide inexpensive ways for storing information for archival and/or distribution purposes.

Central processing unit (CPU) 3904 may be the main processor for software program execution in computing device 3900. CPU 3904 may represent one or more processing units that obtain software instructions from memory module 3906 and execute such instructions to carry out computations and/or transfer data between various sources and destinations of data, such as hard disk 3932, I/O processor 3920, display interface 3914, input devices 3918, non-volatile memory 3924, and the like.

Memory module 3906 may include RAM (Random Access Memory), ROM (Read Only Memory), and other storage means, mapped to one addressable memory space.

Memory module 3906 illustrates one of many types of computer storage media for storage of information such as computer readable instructions, data structures, program modules or other data. Memory module 3906 may store a basic input/output system (BIOS) for controlling low-level operation of computing device 3900. Memory module 3906 may also store OS 3908 for controlling the general operation of computing device 3900. It will be appreciated that OS 3908 may include a general-purpose operating system such as a version of UNIX, or a specialized client-side and/or mobile communication operating system. OS 3908 may, in turn, include or interface with a Java virtual machine (JVM) module that enables control of hardware components and/or operating system operations via Java application programs.

Memory module 3906 may further include one or more distinct areas (by address space and/or other means), which can be utilized by computing device 3900 to store, among other things, applications and/or other data. For example, one area of memory module 3906 may be set aside and employed to store information that describes various capabilities of computing device 3900, a device identifier, and the like. Such identification information may then be provided to another device based on any of a variety of events, including being sent as part of a header during a communication, sent upon request, or the like.

One common software application is a browser program that is generally used to send/receive information to/from a web server. In one embodiment, the browser application is enabled to employ handheld device markup language (HDML), wireless markup language (WML), WMLScript, JavaScript, standard generalized markup language (SMGL), hypertext markup language (HTML), eXtensible markup language (XML), and the like, to display and send a message. Any of a variety of other web based languages may also be employed. In one embodiment, using the browser application, a user may view an article or other content on a web page with one or more highlighted portions as target objects.

Display interface 3914 may be coupled with a display unit 3990, such as liquid crystal display (LCD), gas plasma, light emitting diode (LED), or any other type of display unit that may be used with computing device 3900. Display unit 3990 coupled with display interface 3914 may also include a touch sensitive screen arranged to receive input from an object such as a stylus or a digit from a human hand. Display interface 3914 may further include interface for other visual status indicators, such light emitting diodes (LED), light arrays, and the like. Display interface 3914 may include both hardware and software components. For example, display interface 3914 may include a graphic accelerator for rendering graphic-intensive outputs on the display unit. In one embodiment, display interface 3914 may include software and/or firmware components that work in conjunction with CPU 3904 to render graphic output on the display unit.

Audio interface 3916 is arranged to produce and receive audio signals such as the sound of a human voice. For example, audio interface 3916 may be coupled to a speaker and microphone to enable communication with a human operator, such as spoken commands, and/or generate an audio acknowledgement for some action.

Input devices 3918 may include a variety of device types arranged to receive input from a user, such as a keyboard, a keypad, a mouse, a touchpad, a touch-screen (described with respect to display interface 3914), a multi-touch screen, a microphone for spoken command input (describe with respect to audio interface 3916), and the like.

I/O processor 3920 is generally employed to handle transactions and communications with peripheral devices such as mass storage, network, input devices, display, and the like, which couple computing device 3900 with the external world. In small, low power computing devices, such as some mobile devices, functions of the I/O processor 3920 may be integrated with CPU 3904 to reduce hardware cost and complexity. In one embodiment, I/O processor 3920 may the primary software interface with all other device and/or hardware interfaces, such as optical storage 3902, hard disk 3932, interfaces 3926-3928, display interface 3914, audio interface 3916, and input devices 3918.

An electrical bus 3922 internal to computing device 3900 may be used to couple various other hardware components, such as CPU 3904, memory module 3906, I/O processor 3920, and the like, to each other for transferring data, instructions, status, and other similar information.

Non-volatile memory 3924 may include memory built into computing device 3900, or portable storage medium, such as USB drives that may include PCM arrays, flash memory including NOR and NAND flash, pluggable hard drive, and the like. In one embodiment, portable storage medium may behave similarly to a disk drive. In another embodiment, portable storage medium may present an interface different than a disk drive, for example, a read-only interface used for loading/supplying data and/or software.

Various other interfaces 3926-3928 may include other electrical and/or optical interfaces for connecting to various hardware peripheral devices and networks, such as IEEE 1394 also known as FireWire, Universal Serial Bus (USB), Small Computer Serial Interface (SCSI), parallel printer interface, Universal Synchronous Asynchronous Receiver Transmitter (USART), Video Graphics Array (VGA), Super VGA (SVGA), and the like.

Network interface card (NIC) 3930 may include circuitry for coupling computing device 3900 to one or more networks, and is generally constructed for use with one or more communication protocols and technologies including, but not limited to, global system for mobile communication (GSM), code division multiple access (CDMA), time division multiple access (TDMA), user datagram protocol (UDP), transmission control protocol/Internet protocol (TCP/IP), SMS, general packet radio service (GPRS), WAP, ultra wide band (UWB), IEEE 802.16 Worldwide Interoperability for Microwave Access (WiMax), SIP/RTP, Bluetooth, Wi-Fi, Zigbee, UMTS, HSDPA, WCDMA, WEDGE, or any of a variety of other wired and/or wireless communication protocols.

Hard disk 3932 is generally used as a mass storage device for computing device 3900. In one embodiment, hard disk 3932 may be a Ferro-magnetic stack of one or more disks forming a disk drive embedded in or coupled to computing device 3900. Alternatively, hard drive 3932 may be implemented as a solid-state device configured to behave as a disk drive, such as a flash-based hard drive. In yet another embodiment, hard drive 3932 may be a remote storage accessible over network interface 3930 or another interface 3926, but acting as a local hard drive.

Power supply 3934 provides power to computing device 3900. A rechargeable or non-rechargeable battery may be used to provide power. The power may also be provided by an external power source, such as an AC adapter or a powered docking cradle that supplements and/or recharges a battery.

Transceiver 3936 generally represents transmitter/receiver circuits for wired and/or wireless transmission and receipt of electronic data. Transceiver 3936 may be a stand-alone module or be integrated with other modules, such as NIC 3930. Transceiver 3936 may be coupled with one or more antennas for wireless transmission of information.

Antenna 3938 is generally used for wireless transmission of information, for example, in conjunction with transceiver 3936, NIC 3930, and/or GPS 3942. Antenna 3938 may represent one or more different antennas that may be coupled with different devices and tuned to different carrier frequencies configured to communicate using corresponding protocols and/or networks. Antenna 3938 may be of various types, such as omni-directional, dipole, slot, helical, and the like.

Haptic interface 3940 is configured to provide tactile feedback to a user of computing device 3900. For example, the haptic interface may be employed to vibrate computing device 3900, or an input device coupled to computing device 3900. For example, when a message is received by device 3900 or another event occurs, the device may vibrate to alert the user.

Global positioning system (GPS) unit 3942 can determine the physical coordinates of computing device 3900 on the surface of the Earth, which typically outputs a location as latitude and longitude values. GPS unit 3942 can also employ other geo-positioning mechanisms, including, but not limited to, triangulation, assisted GPS (AGPS), E-OTD, CI, SAI, ETA, BSS or the like, to further determine the physical location of computing device 3900 on the surface of the Earth. It is understood that under different conditions, GPS unit 3942 can determine a physical location within millimeters for computing device 3900. In other cases, the determined physical location may be less precise, such as within a meter or significantly greater distances. In one embodiment, however, a mobile device represented by computing device 3900 may, through other components, provide other information that may be employed to determine a physical location of the device, including for example, a MAC address.

Using instructions stored in memory module 3906, device 3900 may read the instructions to have CPU 3904 execute the functions specified in the instructions. These functions are disclosed in greater detail by FIGS. 3A, 3B and 4. Thus, computing device 3900 is configured to be a special purpose device for managing collaborative credentialing, compliance, and scheduling of contingent healthcare workers by multiple MSPs and healthcare facilities.

It will be apparent to those skilled in the art that various modifications and variations can be made in the disclosed embodiments of the disclosed device and associated methods without departing from the spirit or scope of the invention. Thus, it is intended that the present invention covers the modifications and variations of the embodiments disclosed above provided that the modifications and variations come within the scope of any claims and their equivalents.

What is claimed is:

1. A computerized method for managing a managed service provider (MSP) platform, the method comprising:
   providing a central processing unit communicatively connected to an MSP server computer;
   providing memory for storing data, wherein the memory is communicatively connected to the central processing unit and the MSP server computer;
   executing instructions stored in the memory and causing the central processing unit to perform the steps of
   a) creating a computerized electronic marketplace platform on the MSP server computer, wherein the computerized electronic marketplace platform is displayed as an MSP user interface on a display connected to the MSP server computer;
   b) creating digital profiles for a plurality of healthcare facilities on the computerized marketplace electronic platform, wherein each digital profile includes customized data that is healthcare facility-specific and represents one or more departments and healthcare management needs for the healthcare facility;
   c) storing the digital profiles for a plurality of healthcare facilities in the memory;
   d) the central processing unit electronically authorizing the healthcare facility's electronic access to the computerized marketplace electronic platform, wherein access is provided only after the healthcare facility's digital profile is created in the computerized marketplace electronic platform, once access is provided, the electronic marketplace platform is displayed as a customer user interface on a display of an electronic device that is associated with the healthcare facility;
   e) electronically onboarding a healthcare facility from the plurality of healthcare facilities onto the computerized electronic marketplace platform, wherein the healthcare facility onboarding process comprises automatically configuring the healthcare facility into a plurality of groups, wherein the groups include shift types, departments, credentialing, and compliance, wherein each group includes a plurality of data elements, wherein the configuring is performed dynamically to accommodate any real-time changes to data elements of each group;
   f) authorizing the healthcare facility's access to features of the computerized marketplace electronic platform, wherein, one of the features includes an electronic broadcast mechanism that allows the healthcare facility to broadcast an announcement or a job order to one or more suppliers associated with the computerized marketplace electronic platform;
   g) creating a digital profile for each of the suppliers from the plurality of suppliers on the computerized marketplace electronic platform, wherein the digital profile includes customized data that is supplier-specific and represents the supplier's services and healthcare workers provided by the supplier;
   h) storing the digital profiles of the plurality of suppliers in the memory;
   i) electronically authorizing the plurality of supplier's electronic access to the computerized marketplace electronic platform, wherein access is provided only after the supplier's digital profile is created in the computerized marketplace electronic platform, once access is provided, the electronic marketplace platform is displayed as a supplier user interface on a display of a supplier electronic device;
   j) electronically onboarding the plurality of suppliers and providing them access to features of the computerized marketplace electronic platform, wherein one of the features includes receiving a broadcasted announcement or a job order;
   k) autonomously mapping the plurality of onboarded suppliers to the plurality of onboarded healthcare facilities based on the requirements outlined by each onboarded healthcare facility wherein, the autonomous mapping process comprises
   the central processing unit creating a healthcare facility-supplier mapping checklist for each of the onboarded healthcare facilities, wherein each healthcare facility-supplier mapping checklist is specific to a healthcare facility, wherein each healthcare facility-supplier mapping checklist includes a plurality of requirements for a supplier to be placed on their approved supplier list, wherein one of the requirements is a supplier background check, wherein another requirement is a supplier compliance check, the central processing unit executing the healthcare facility-supplier mapping checklist and mapping an onboarded supplier to a healthcare facility upon the supplier satisfying all the requirements of the healthcare facility's mapping checklist;

l) creating a customized approved supplier list for each of the onboarded healthcare facilities, wherein the approved supplier list includes only those onboarded suppliers that satisfy all the requirements of the healthcare facility-supplier mapping checklist;

m) using the broadcast mechanism, broadcasting a specific job opening for one of the onboarded healthcare facilities, wherein the healthcare facility is provided the option to broadcast the job opening to the entire customized approved supplier list or select a subset of suppliers from the customized approved supplier list;

n) the healthcare facility receiving a response to the job opening by one or more of the suppliers to whom the job opening was broadcasted, wherein the response to job opening includes an electronically creating digital profile of one or more healthcare workers that are associated with the supplier, wherein each healthcare worker digital profile contains meta data;

o) storing the created healthcare worker digital profile in memory;

p) the healthcare facility selecting one or more of the healthcare workers associated with the supplier on the approved supplier list, wherein the supplier associated with the healthcare worker places the healthcare worker in a plurality of queues such that the healthcare worker can accept additional job orders from other healthcare facilities;

q) upon selection of the healthcare worker by the healthcare facility, the central processing unit activating a real-time computerized negotiator tool, wherein the computerized negotiator tool allows real-time back and forth negotiation between the supplier and the matched healthcare facility, wherein the negotiation is related to the compensation of the healthcare worker, wherein the negotiation is repeated until either an agreement or a denial is reached between the approved supplier and the onboarded healthcare facility;

r) upon selection of the healthcare worker by the healthcare facility, the central processing unit automatically activating a compliance manager, wherein the central processing unit causes the compliance manager to performs the steps of dynamically constructing an electronic healthcare compliance electronic checklist, wherein the checklist includes a plurality of compliance requirements, automatically reviewing the selected healthcare worker's documents to verify compliance with each of the compliance requirements, automatically marking each requirement as verified or missing, in real-time, automatically notifying the healthcare worker or the supplier that represents the healthcare worker of the missing requirements, wherein such alert is an electronic communication sent to an electronic device of the healthcare worker or the supplier that represents the healthcare worker, wherein upon determining that a requirement is missing, the compliance manager automatically starts an electronic tracking process, wherein the tracking process sends reminders to the healthcare worker or the supplier for submitting the missing document and ends tracking when the missing document is submitted;

s) upon selection of the healthcare worker by the healthcare facility, dynamically preventing collision of submission, wherein the dynamic prevention includes automatically blocking the healthcare worker profile such that another supplier cannot submit the same healthcare worker profile to the same healthcare facility;

t) upon selection of the healthcare worker by the healthcare facility, analyzing in real-time, changing schedule of the healthcare worker and the changing shift openings at the healthcare facility, to dynamically map the healthcare worker schedule with the shift opening at the healthcare facility, wherein the system analyses the changing schedule and the changing shift opening periodically thereby resulting in assigning of a specific shift to the healthcare worker; and u) upon assignment of a shift to the healthcare worker, dynamically blocking the time slot associated with the shift such that the healthcare worker cannot be submitted for another shift or another job order for the same time slot.

2. The computerized method of claim 1, wherein the supplier from the approved supplier list builds the digital profiles of the healthcare workers and stores it on a database connected to the supplier's electronic device, wherein the profile is built by a processor of the electronic device performing the steps of tracking a plurality of worker onboarding queues, wherein the plurality of queues includes a screening queue, an interviewer queue, an offer queue, a compliance manager queue, an administrator queue, an orientation scheduling queue, and an orientation verification queue.

3. The computerized method of claim 1, wherein the central processing unit causes the compliance manager to routinely perform the step of verifying all compliance related documents for the healthcare facility and the supplier stored in the memory of the server computer.

4. The computerized method of claim 3, wherein the compliance manager dynamically determines adherence verification of all compliance related documents and approves the healthcare worker to work a shift at the healthcare facility only upon completion of all required compliance documents.

5. The computerized method of claim 3, wherein the compliance manager performs the steps of:

dynamically generating a complete list of all required credentials, wherein the list of required credentials are specifically configured for each healthcare facility that are needed for approval of the healthcare worker, dynamically retrieving past performance reviews of the healthcare worker and placing them on the electronic platform, electronically and automatically comparing the required list of credentials and health compliance documents with a subset of credentials and health compliance documents already received by the healthcare facility, electronically and automatically identifying the missing set of credentials and health compliance documents based on the comparison performed, and electronically and automatically alerting an agency responsible for the healthcare worker to submit only those credentials and health compliance documents that are deemed missing and would make the list complete for approval.

6. The computerized method of claim 5, wherein the required list of credentials for approving the healthcare worker include is the current status of their license, certifications, and health compliance to provide medical care.

7. The computerized method of claim 5, wherein the past performance reviews of the healthcare worker include ratings and comments relating to the healthcare worker's past performance, wherein the requirement for approving the healthcare worker is evaluating healthcare worker's past work performance through the reviews and ratings.

8. The computerized method of claim 1, wherein the compliance manager in real-time determines any missing information or bottlenecks in the selection of the healthcare worker by the healthcare facility to allow visibility and real-time ability to solve any delay in the selection of the healthcare worker by the healthcare facility thereby resulting approval of the healthcare worker without delays due to the missing information or bottlenecks.

9. A physical and tangible computer readable medium for storing non-transitory computer readable instructions, the computer readable instructions performing a method for creating and managing a managed service provider (MSP) platform when executed by one or more processing devices, the method comprising:

providing a central processing unit communicatively connected to an MSP server computer;

providing memory for storing data, wherein the memory is communicatively connected to the central processing unit and the MSP server computer;

executing instructions stored in the memory and causing the central processing unit to perform the steps of a) creating a computerized electronic marketplace platform on the MSP server computer, wherein the computerized electronic marketplace platform is displayed as an MSP user interface on a display connected to the MSP server computer;

b) creating digital profiles for a plurality of healthcare facilities on the computerized marketplace electronic platform, wherein each digital profile includes customized data that is healthcare facility-specific and represents one or more departments and healthcare management needs for the healthcare facility;

c) storing the digital profiles for a plurality of healthcare facilities in the memory;

d) the central processing unit electronically authorizing the healthcare facility's electronic access to the computerized marketplace electronic platform, wherein access is provided only after the healthcare facility's digital profile is created in the computerized marketplace electronic platform, once access is provided, the electronic marketplace platform is displayed as a customer user interface on a display of an electronic device that is associated with the healthcare facility;

e) electronically onboarding a healthcare facility from the plurality of healthcare facilities onto the computerized electronic marketplace platform, wherein the healthcare facility onboarding process comprises automatically configuring the healthcare facility into a plurality of groups, wherein the groups include shift types, departments, credentialing, and compliance, wherein each group includes a plurality of data elements, wherein the configuring is performed dynamically to accommodate any real-time changes to data elements of each group;

f) authorizing the healthcare facility's access to features of the computerized marketplace electronic platform, wherein, one of the features includes an electronic broadcast mechanism that allows the healthcare facility to broadcast an announcement or a job order to one or more suppliers associated with the computerized marketplace electronic platform;

g) creating a digital profile for each of the suppliers from the plurality of suppliers on the computerized marketplace electronic platform, wherein the digital profile includes customized data that is supplier-specific and represents the supplier's services and healthcare workers provided by the supplier;

h) storing the digital profiles of the plurality of suppliers in the memory;

i) electronically authorizing the plurality of supplier's electronic access to the computerized marketplace electronic platform, wherein access is provided only after the supplier's digital profile is created in the computerized marketplace electronic platform, once access is provided, the electronic marketplace platform is displayed as a supplier user interface on a display of a supplier electronic device;

j) electronically onboarding the plurality of suppliers and providing them access to features of the computerized marketplace electronic platform, wherein one of the features includes receiving a broadcasted announcement or a job order;

k) autonomously mapping the plurality of onboarded suppliers to the plurality of onboarded healthcare facilities based on the requirements outlined by each onboarded healthcare facility wherein, the autonomous mapping process comprises the central processing unit creating a healthcare facility-supplier mapping checklist for each of the onboarded healthcare facilities, wherein each healthcare facility-supplier mapping checklist is specific to a healthcare facility, wherein each healthcare facility-supplier mapping checklist includes a plurality of requirements for a supplier to be placed on their approved supplier list, wherein one of the requirements is a supplier background check, wherein another requirement is a supplier compliance check, the central processing unit executing the healthcare facility-supplier mapping checklist and mapping an onboarded supplier to a healthcare facility upon the supplier satisfying all the requirements of the healthcare facility's mapping checklist;

l) creating a customized approved supplier list for each of the onboarded healthcare facilities, wherein the approved supplier list includes only those onboarded suppliers that satisfy all the requirements of the healthcare facility-supplier mapping checklist;

m) using the broadcast mechanism, broadcasting a specific job opening for one of the onboarded healthcare facilities, wherein the healthcare facility is provided the option to broadcast the job opening to the entire customized approved supplier list or select a subset of suppliers from the customized approved supplier list;

n) the healthcare facility receiving a response to the job opening by one or more of the suppliers to whom the job opening was broadcasted, wherein the response to job opening includes an electronically creating digital profile of one or more healthcare workers that are associated with the supplier, wherein each healthcare worker digital profile contains meta data;

o) storing the created healthcare worker digital profile in memory;

p) the healthcare facility selecting one or more of the healthcare workers associated with the supplier on the approved supplier list, wherein the supplier associated with the healthcare worker places the healthcare worker in a plurality of queues such that the healthcare worker can accept additional job orders from other healthcare facilities;

q) upon selection of the healthcare worker by the healthcare facility, the central processing unit activating a real-time computerized negotiator tool, wherein the computerized negotiator tool allows real-time back and forth negotiation between the supplier and the matched healthcare facility, wherein the negotiation is related to the compensation of the healthcare worker, wherein the negotiation is repeated until either an agreement or a denial is reached between the approved supplier and the onboarded healthcare facility;

r) upon selection of the healthcare worker by the healthcare facility, the central processing unit automatically activating a compliance manager, wherein the central processing unit causes the compliance manager to performs the steps of dynamically constructing an electronic healthcare compliance electronic checklist, wherein the checklist includes a plurality of compliance requirements, automatically reviewing the selected healthcare worker's documents to verify compliance with each of the compliance requirements, automatically marking each requirement as verified or missing, in real-time, automatically notifying the healthcare worker or the supplier that represents the healthcare worker of the missing requirements, wherein such alert is an electronic communication sent to an electronic device of the healthcare worker or the supplier that represents the healthcare worker, wherein upon determining that a requirement is missing, the compliance manager automatically starts an electronic tracking process, wherein the tracking process sends reminders to the healthcare worker or the supplier for submitting the missing document and ends tracking when the missing document is submitted;

s) upon selection of the healthcare worker by the healthcare facility, dynamically preventing collision of submission, wherein the dynamic prevention includes automatically blocking the healthcare worker profile such that another supplier cannot submit the same healthcare worker profile to the same healthcare facility;

t) upon selection of the healthcare worker by the healthcare facility, analyzing in real-time, changing schedule of the healthcare worker and the changing shift openings at the healthcare facility, to dynamically map the healthcare worker schedule with the shift opening at the healthcare facility, wherein the system analyses the changing schedule and the changing shift opening periodically thereby resulting in assigning of a specific shift to the healthcare worker; and u) upon assignment of a shift to the healthcare worker, dynamically blocking the time slot associated with the shift such that the healthcare worker cannot be submitted for another shift or another job order for the same time slot.

10. The physical and tangible computer readable medium of claim 9, wherein the supplier from the approved supplier list builds the digital profiles of the healthcare workers and stores it on a database connected to the supplier's electronic device, wherein the profile is built by a processor of the electronic device performing the steps of tracking a plurality of worker onboarding queues, wherein the plurality of queues includes a screening queue, an interviewer queue, an offer queue, a compliance manager queue, an administrator queue, an orientation scheduling queue, and an orientation verification queue.

11. The physical and tangible computer readable medium of claim 9, wherein the compliance manager verifies all compliance related documents for a specific set of healthcare facilities and its suppliers.

12. The physical and tangible computer readable medium of claim 9, wherein the compliance manager dynamically determines adherence to all required compliance policies and procedures and approves a healthcare worker to work a shift at the healthcare facility only upon successful conformance.

13. The physical and tangible computer readable medium of claim 9, wherein the compliance manager performs the steps of:

dynamically generating a complete list of all required credentials, wherein the list of required credentials are specifically configured for each healthcare facility that are needed for approval of the healthcare worker, dynamically retrieving past performance reviews of the healthcare worker and placing them on the electronic platform, electronically and automatically comparing the required list of credentials and health compliance documents with a subset of credentials and health compliance documents already received by the healthcare facility, electronically and automatically identifying the missing set of credentials and health compliance documents based on the comparison performed, and electronically and automatically alerting an agency responsible for the healthcare worker to submit only those credentials and health compliance documents that are deemed missing and would make the list complete for approval.

14. The physical and tangible computer readable medium of claim 13, wherein the required list of credentials for approving the healthcare worker include the current status of their license, certifications, and health compliance to provide medical care.

15. The physical and tangible computer readable medium of claim 13, wherein the past performance reviews of the healthcare worker include ratings and comments relating to the healthcare worker's past performance, wherein the requirement for approving the healthcare worker is evaluating healthcare worker's past work performance through the reviews and ratings.

16. The physical and tangible computer readable medium of claim 13, wherein the compliance manager electronically produces a compliance report.

17. The physical and tangible computer readable medium of claim 16, wherein the compliance report acts as legal proof that all requirements and governance for the healthcare worker have been completed.

18. The physical and tangible computer readable medium of claim 9, wherein the compliance manager maintains the status of healthcare worker's immunizations and its expiration.

19. The physical and tangible computer readable medium of claim 9, wherein the compliance manager dynamically creates an electronic audit and health menu relating to audit and health services acceptance processes.

20. The physical and tangible computer readable medium of claim 9, wherein the compliance manager in real-time determines any missing information or bottlenecks in the selection of the healthcare worker by the healthcare facility to allow visibility and real-time ability to solve any delay in the selection of the healthcare worker by the healthcare facility thereby resulting approval of the healthcare worker without delays due to the missing information or bottlenecks.

\* \* \* \* \*